(12) United States Patent
Mernoe

(10) Patent No.: US 8,597,244 B2
(45) Date of Patent: *Dec. 3, 2013

(54) INFUSION PUMP SYSTEM, AN INFUSION PUMP UNIT AND AN INFUSION PUMP

(75) Inventor: Morten Mernoe, Charlottenlund (DK)

(73) Assignee: Asante Solutions, Inc., Sunnyvale, CA (US)

( * ) Notice: Subject to any disclaimer, the term of this patent is extended or adjusted under 35 U.S.C. 154(b) by 1278 days.

This patent is subject to a terminal disclaimer.

(21) Appl. No.: 11/738,311

(22) Filed: Apr. 20, 2007

(65) Prior Publication Data

US 2007/0201992 A1 Aug. 30, 2007

Related U.S. Application Data

(63) Continuation of application No. 11/041,189, filed on Jan. 21, 2005, now Pat. No. 7,232,423, which is a continuation of application No. PCT/DK03/00507, filed on Jul. 21, 2003.

(30) Foreign Application Priority Data

Jul. 24, 2002 (DK) .................................. 2002 01133

(51) Int. Cl.
*A61M 5/20* (2006.01)
*A61M 37/00* (2006.01)
*A61M 1/00* (2006.01)

(52) U.S. Cl.
USPC ............ 604/135; 604/134; 604/151; 604/154

(58) Field of Classification Search
USPC ......... 604/220, 207–210, 218, 131, 134, 135, 604/151, 154, 155
See application file for complete search history.

(56) References Cited

U.S. PATENT DOCUMENTS

| | | | |
|---|---|---|---|
| 1,718,596 A * | 6/1929 | Smith | .......................... 604/223 |
| 2,605,765 A | 8/1952 | Kollsman | |
| 3,886,938 A | 6/1975 | Szabo et al. | |
| 4,077,405 A | 3/1978 | Haerten et al. | |
| 4,231,368 A | 11/1980 | Becker | |
| 4,265,241 A | 5/1981 | Portner et al. | |
| 4,300,554 A | 11/1981 | Hessberg et al. | |
| 4,313,439 A * | 2/1982 | Babb et al. | ...................... 604/28 |
| 4,398,908 A | 8/1983 | Siposs | |
| 4,435,173 A | 3/1984 | Siposs et al. | |
| 4,443,218 A | 4/1984 | DeCant, Jr. et al. | |

(Continued)

FOREIGN PATENT DOCUMENTS

DE 196 27 619 1/1989
DE 102 36 669 2/2004

(Continued)

OTHER PUBLICATIONS

U.S. Appl. No. 11/362,616.

(Continued)

*Primary Examiner* — Kevin C Sirmons
*Assistant Examiner* — Andrew Gilbert
(74) *Attorney, Agent, or Firm* — Fish & Richardson P.C.

(57) ABSTRACT

An infusion pump unit includes a housing sized to allow the pump unit to be carried as a portable unit. The housing contains a controllable pumping system for pumping fluid. The pump actuator is lighter, smaller, quieter and less power consuming.

28 Claims, 17 Drawing Sheets

(56) References Cited

U.S. PATENT DOCUMENTS

| | | | |
|---|---|---|---|
| 4,493,704 A | 1/1985 | Beard et al. | |
| 4,529,401 A | 7/1985 | Leslie et al. | |
| 4,562,751 A * | 1/1986 | Nason et al. | 74/111 |
| 4,685,903 A * | 8/1987 | Cable et al. | 604/154 |
| 4,850,817 A | 7/1989 | Nason et al. | |
| 4,921,487 A * | 5/1990 | Buffet et al. | 604/135 |
| 5,045,064 A | 9/1991 | Idriss | |
| 5,088,981 A | 2/1992 | Howson et al. | |
| 5,190,522 A | 3/1993 | Wojcicki et al. | |
| 5,250,027 A | 10/1993 | Lewis et al. | |
| 5,261,882 A | 11/1993 | Sealfon et al. | |
| 5,314,412 A | 5/1994 | Rex | |
| 5,335,994 A | 8/1994 | Weynant nee Girones | |
| 5,338,157 A | 8/1994 | Blomquist | |
| 5,342,180 A | 8/1994 | Daoud | |
| 5,395,340 A | 3/1995 | Lee | |
| 5,411,487 A | 5/1995 | Castagna | |
| 5,545,143 A | 8/1996 | Fischell et al. | |
| 5,551,850 A | 9/1996 | Williamson et al. | |
| 5,569,186 A | 10/1996 | Lord et al. | |
| 5,626,566 A | 5/1997 | Petersen et al. | |
| 5,637,095 A | 6/1997 | Nason et al. | |
| 5,665,065 A | 9/1997 | Colman et al. | |
| 5,741,216 A | 4/1998 | Hemmingsen et al. | |
| 5,772,635 A | 6/1998 | Dastur et al. | |
| 5,816,306 A | 10/1998 | Giacomel | |
| 5,852,803 A | 12/1998 | Ashby, III et al. | |
| 5,919,167 A | 7/1999 | Mulhauser et al. | |
| 5,925,018 A | 7/1999 | Ungerstedt | |
| 5,928,201 A | 7/1999 | Poulsen et al. | |
| 5,947,934 A | 9/1999 | Hansen et al. | |
| 5,951,530 A | 9/1999 | Steengaard et al. | |
| 5,957,889 A | 9/1999 | Poulsen et al. | |
| 5,984,894 A | 11/1999 | Poulsen et al. | |
| 5,984,897 A | 11/1999 | Petersen et al. | |
| 5,997,475 A | 12/1999 | Bortz | |
| 6,003,736 A | 12/1999 | Ljunggren | |
| 6,010,485 A | 1/2000 | Buch-Rasmussen et al. | |
| 6,033,377 A | 3/2000 | Rasmussen et al. | |
| 6,045,537 A | 4/2000 | Klitmose | |
| 6,074,372 A | 6/2000 | Hansen | |
| 6,110,149 A | 8/2000 | Klitgaard et al. | |
| 6,156,014 A | 12/2000 | Petersen et al. | |
| 6,171,276 B1 | 1/2001 | Lippe et al. | |
| 6,231,540 B1 | 5/2001 | Smedegaard | |
| 6,248,067 B1 | 6/2001 | Causey, III et al. | |
| 6,248,090 B1 | 6/2001 | Jensen et al. | |
| 6,248,093 B1 | 6/2001 | Moberg | |
| 6,277,098 B1 | 8/2001 | Klitmose et al. | |
| 6,302,855 B1 | 10/2001 | Lav et al. | |
| 6,302,869 B1 | 10/2001 | Klitgaard | |
| 6,375,638 B2 | 4/2002 | Nason et al. | |
| 6,379,339 B1 | 4/2002 | Klitgaard et al. | |
| 6,381,496 B1 | 4/2002 | Meadows et al. | |
| 6,404,098 B1 | 6/2002 | Kayama et al. | |
| 6,427,088 B1 | 7/2002 | Bowman, IV et al. | |
| 6,461,331 B1 | 10/2002 | Van Antwerp | |
| 6,474,219 B2 | 11/2002 | Klitmose et al. | |
| 6,485,461 B1 | 11/2002 | Mason et al. | |
| 6,508,788 B2 | 1/2003 | Preuthun | |
| 6,524,280 B2 | 2/2003 | Hansen et al. | |
| 6,533,183 B2 | 3/2003 | Aasmul et al. | |
| 6,537,251 B2 | 3/2003 | Klitmose | |
| 6,540,672 B1 | 4/2003 | Simonsen et al. | |
| 6,544,229 B1 | 4/2003 | Danby et al. | |
| 6,547,764 B2 | 4/2003 | Larsen et al. | |
| 6,551,276 B1 | 4/2003 | Mann et al. | |
| 6,554,798 B1 | 4/2003 | Mann et al. | |
| 6,554,800 B1 * | 4/2003 | Nezhadian et al. | 604/152 |
| 6,558,320 B1 | 5/2003 | Causey, III et al. | |
| 6,558,351 B1 | 5/2003 | Steil et al. | |
| 6,562,001 B2 | 5/2003 | Lebel et al. | |
| 6,562,011 B1 | 5/2003 | Buch-Rasmussen et al. | |
| 6,564,105 B2 | 5/2003 | Starkweather et al. | |
| 6,569,126 B1 | 5/2003 | Poulsen et al. | |
| 6,571,128 B2 | 5/2003 | Lebel et al. | |
| 6,577,899 B2 | 6/2003 | Lebel et al. | |
| 6,582,404 B1 | 6/2003 | Klitgaard et al. | |
| 6,585,644 B2 | 7/2003 | Lebel et al. | |
| 6,585,699 B2 | 7/2003 | Ljunggreen et al. | |
| 6,605,067 B1 | 8/2003 | Larsen | |
| 6,613,019 B2 | 9/2003 | Munk | |
| 6,641,533 B2 | 11/2003 | Causey, III et al. | |
| 6,648,821 B2 | 11/2003 | Lebel et al. | |
| 6,650,951 B1 | 11/2003 | Jones et al. | |
| 6,656,158 B2 * | 12/2003 | Gregory et al. | 604/131 |
| 6,656,159 B2 * | 12/2003 | Flaherty | 604/131 |
| 6,659,948 B2 | 12/2003 | Lebel et al. | |
| 6,659,978 B1 | 12/2003 | Kasuga et al. | |
| 6,659,980 B2 | 12/2003 | Moberg et al. | |
| 6,663,602 B2 | 12/2003 | Møller | |
| 6,668,196 B1 | 12/2003 | Villegas et al. | |
| 6,669,669 B2 | 12/2003 | Flaherty et al. | |
| 6,687,546 B2 | 2/2004 | Lebel et al. | |
| 6,690,192 B1 | 2/2004 | Wing | |
| 6,691,043 B2 | 2/2004 | Ribeiro, Jr. | |
| 6,692,457 B2 | 2/2004 | Flaherty | |
| 6,692,472 B2 | 2/2004 | Hansen et al. | |
| 6,694,191 B2 | 2/2004 | Starkweather et al. | |
| 6,699,218 B2 | 3/2004 | Flaherty et al. | |
| 6,702,779 B2 | 3/2004 | Connelly et al. | |
| 6,715,516 B2 | 4/2004 | Ohms et al. | |
| 6,716,198 B2 | 4/2004 | Larsen | |
| 6,723,072 B2 | 4/2004 | Flaherty et al. | |
| 6,733,446 B2 | 5/2004 | Lebel et al. | |
| 6,736,796 B2 | 5/2004 | Shekalim | |
| 6,740,059 B2 | 5/2004 | Flaherty | |
| 6,740,072 B2 | 5/2004 | Starkweather et al. | |
| 6,740,075 B2 | 5/2004 | Lebel et al. | |
| 6,744,350 B2 | 6/2004 | Blomquist | |
| 6,749,587 B2 | 6/2004 | Flaherty | |
| 6,752,787 B1 | 6/2004 | Causey, III et al. | |
| 6,758,810 B2 | 7/2004 | Lebel et al. | |
| 6,768,425 B2 | 7/2004 | Flaherty et al. | |
| 6,780,156 B2 | 8/2004 | Haueter et al. | |
| 6,786,246 B2 | 9/2004 | Ohms et al. | |
| 6,786,890 B2 | 9/2004 | Preuthun et al. | |
| 6,796,970 B1 | 9/2004 | Klitmose et al. | |
| 6,799,149 B2 | 9/2004 | Hartlaub | |
| 6,809,653 B1 | 10/2004 | Mann et al. | |
| 6,810,290 B2 | 10/2004 | Lebel et al. | |
| 6,811,533 B2 | 11/2004 | Lebel et al. | |
| 6,811,534 B2 | 11/2004 | Bowman, IV et al. | |
| 6,813,519 B2 | 11/2004 | Lebel et al. | |
| 6,827,702 B2 | 12/2004 | Lebel et al. | |
| 6,830,558 B2 | 12/2004 | Flaherty et al. | |
| 6,852,104 B2 | 2/2005 | Blomquist | |
| 6,854,620 B2 | 2/2005 | Ramey | |
| 6,854,653 B2 | 2/2005 | Eilersen | |
| 6,855,129 B2 | 2/2005 | Jensen et al. | |
| 6,872,200 B2 | 3/2005 | Mann et al. | |
| 6,873,268 B2 | 3/2005 | Lebel et al. | |
| 6,878,132 B2 | 4/2005 | Kipfer | |
| 6,893,415 B2 | 5/2005 | Madsen et al. | |
| 6,899,695 B2 | 5/2005 | Herrera | |
| 6,899,699 B2 | 5/2005 | Enggaard | |
| 6,922,590 B1 | 7/2005 | Whitehurst | |
| 6,936,006 B2 | 8/2005 | Sabra | |
| 6,936,029 B2 | 8/2005 | Mann et al. | |
| 6,945,961 B2 | 9/2005 | Miller et al. | |
| 6,948,918 B2 | 9/2005 | Hansen | |
| 6,950,708 B2 | 9/2005 | Bowman IV et al. | |
| 6,960,192 B1 | 11/2005 | Flaherty et al. | |
| 6,979,326 B2 | 12/2005 | Mann et al. | |
| 6,997,911 B2 | 2/2006 | Klitmose | |
| 6,997,920 B2 | 2/2006 | Mann et al. | |
| 7,005,078 B2 | 2/2006 | Van Lintel et al. | |
| 7,008,399 B2 | 3/2006 | Larson et al. | |
| 7,014,625 B2 | 3/2006 | Bengtsson | |
| 7,018,360 B2 | 3/2006 | Flaherty et al. | |
| 7,025,743 B2 | 4/2006 | Mann | |
| 7,029,455 B2 | 4/2006 | Flaherty | |
| 7,054,836 B2 | 5/2006 | Christensen et al. | |
| 7,104,972 B2 | 9/2006 | Møller et al. | |

(56) References Cited

U.S. PATENT DOCUMENTS

| | | |
|---|---|---|
| 7,128,727 B2 | 10/2006 | Flaherty et al. |
| 7,133,329 B2 | 11/2006 | Skyggebjerg et al. |
| 7,144,384 B2 * | 12/2006 | Gorman et al. ............... 604/131 |
| 7,232,423 B2 * | 6/2007 | Mernoe ........................ 604/135 |
| 2001/0056262 A1 | 12/2001 | Cabiri |
| 2002/0004651 A1 | 1/2002 | Ljndggreen et al. |
| 2002/0007154 A1 | 1/2002 | Hansen et al. |
| 2002/0040208 A1 | 4/2002 | Flaherty et al. |
| 2002/0091358 A1 | 7/2002 | Klitmose |
| 2002/0126036 A1 | 9/2002 | Flaherty et al. |
| 2003/0055380 A1 | 3/2003 | Flaherty |
| 2003/0065308 A1 | 4/2003 | Lebel et al. |
| 2003/0088238 A1 | 5/2003 | Poulsen |
| 2003/0199825 A1 * | 10/2003 | Flaherty ........................ 604/155 |
| 2003/0216683 A1 | 11/2003 | Shekalim |
| 2004/0010207 A1 | 1/2004 | Flaherty et al. |
| 2004/0064088 A1 | 4/2004 | Gorman et al. |
| 2004/0064096 A1 | 4/2004 | Flaherty et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0092878 A1 | 5/2004 | Flaherty |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0171983 A1 | 9/2004 | Sparks et al. |
| 2004/0176727 A1 | 9/2004 | Shekalim |
| 2004/0204673 A1 | 10/2004 | Flaherty |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0065760 A1 | 3/2005 | Murtfeldt et al. |
| 2005/0090808 A1 | 4/2005 | Malave et al. |
| 2005/0095063 A1 | 5/2005 | Fathallah |
| 2005/0160858 A1 | 7/2005 | Mernoe |
| 2005/0171512 A1 | 8/2005 | Flaherty |
| 2005/0182366 A1 | 8/2005 | Vogt et al. |
| 2005/0192561 A1 | 9/2005 | Mernoe |
| 2005/0203461 A1 | 9/2005 | Flaherty et al. |
| 2005/0215982 A1 | 9/2005 | Malave et al. |
| 2005/0222645 A1 | 10/2005 | Malave et al. |
| 2005/0238507 A1 | 10/2005 | DiIanni et al. |
| 2005/0245878 A1 | 10/2005 | Mernoe |
| 2005/0251097 A1 | 11/2005 | Mernoe |
| 2005/0267402 A1 | 12/2005 | Stewart et al. |
| 2005/0273059 A1 | 12/2005 | Mernoe |
| 2006/0041229 A1 | 2/2006 | Garibotto et al. |
| 2006/0069382 A1 | 3/2006 | Pedersen |
| 2006/0074381 A1 | 4/2006 | Malave et al. |
| 2006/0095014 A1 | 5/2006 | Ethelfeld |
| 2006/0135913 A1 | 6/2006 | Ethelfeld |
| 2006/0142698 A1 | 6/2006 | Ethelfeld |
| 2006/0178633 A1 | 8/2006 | Garibotto et al. |
| 2006/0184119 A1 | 8/2006 | Remde et al. |
| 2006/0200073 A1 | 9/2006 | Radmer et al. |
| 2006/0206054 A1 | 9/2006 | Shekalim |
| 2006/0247581 A1 | 11/2006 | Pedersen et al. |
| 2007/0073228 A1 | 3/2007 | Mernoe et al. |
| 2007/0073236 A1 | 3/2007 | Mernoe et al. |
| 2007/0124002 A1 | 5/2007 | Estes et al. |
| 2007/0156092 A1 | 7/2007 | Estes et al. |
| 2007/0167905 A1 | 7/2007 | Estes et al. |
| 2007/0167912 A1 | 7/2007 | Causey et al. |

FOREIGN PATENT DOCUMENTS

| | | |
|---|---|---|
| EP | 0 580 723 | 10/1995 |
| EP | 0 612 004 | 3/1997 |
| EP | 0 496 141 | 4/1997 |
| EP | 1 045 146 | 10/2000 |
| EP | 1 136 698 | 9/2001 |
| EP | 0 721 358 | 5/2002 |
| EP | 1 177 802 | 9/2004 |
| EP | 1 495 775 | 1/2005 |
| EP | 1 527 792 | 5/2005 |
| FR | 2 585 252 | 1/1987 |
| GB | 747 701 | 4/1956 |
| GB | 2 218 831 | 11/1989 |
| JP | 11-010036 | 1/1999 |
| WO | WO 90/15928 | 12/1990 |
| WO | WO 97/21457 | 6/1997 |
| WO | WO 98/57683 | 12/1998 |
| WO | WO 99/21596 | 5/1999 |
| WO | WO 99/39118 | 8/1999 |
| WO | WO 99/48546 | 9/1999 |
| WO | WO 01/72360 | 10/2001 |
| WO | WO 01/91822 | 12/2001 |
| WO | WO 01/91833 | 12/2001 |
| WO | WO 02/40083 | 5/2002 |
| WO | WO 02/57627 | 7/2002 |
| WO | WO 02/100469 | 12/2002 |
| WO | WO 03/103763 | 12/2003 |
| WO | WO 2004/056412 | 7/2004 |
| WO | WO 2004/110526 | 12/2004 |
| WO | WO 2005/039673 | 5/2005 |
| WO | WO 2005/072794 | 8/2005 |
| WO | WO 2005/072795 | 8/2005 |
| WO | WO 2006/105792 | 10/2006 |
| WO | WO 2006/105793 | 10/2006 |
| WO | WO 2006/105794 | 10/2006 |

OTHER PUBLICATIONS

Medtronic News Release, "Medtronic Receives FDA Approval for World's First Insulin Pump with Real-time Continuous Glucose Monitoring," Apr. 13, 2006, 3 pages.

Debiotech News Release, "Debiotech reveals its new miniaturized Disposable Insulin Nanopump™ for Diabetes therapy," available at http://www.debiotech.com/news/nw_159.html Apr. 24, 2006, 3 pages.

Collins and Lee, "Microfluidic flow transducer based on the measurement of electrical admittance," *Lab Chip*, 2004, 4:7-10.

\* cited by examiner

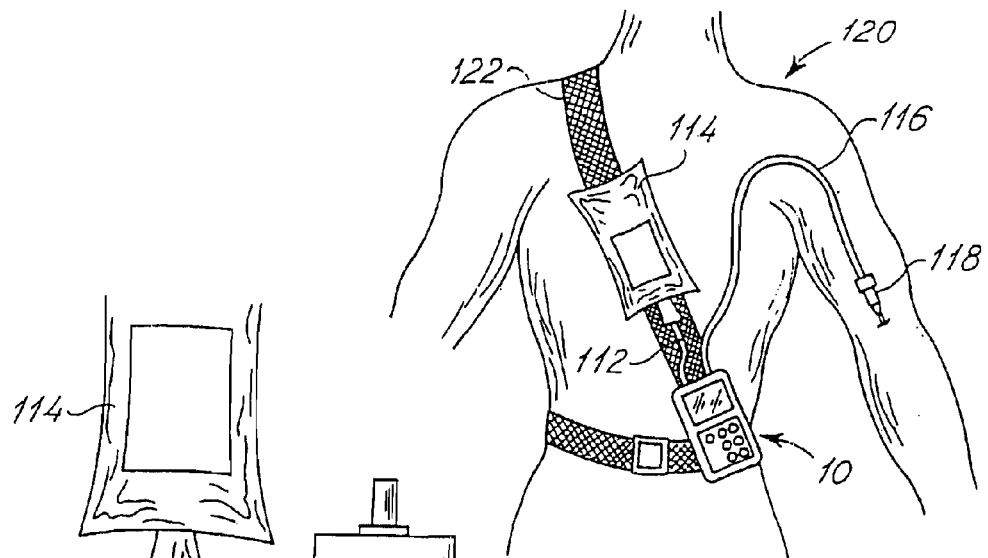
Fig. 4
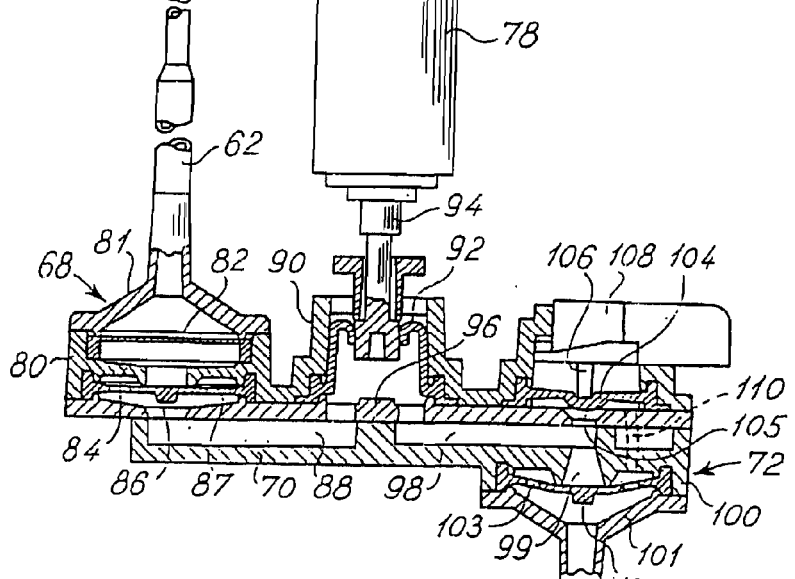
Fig. 3

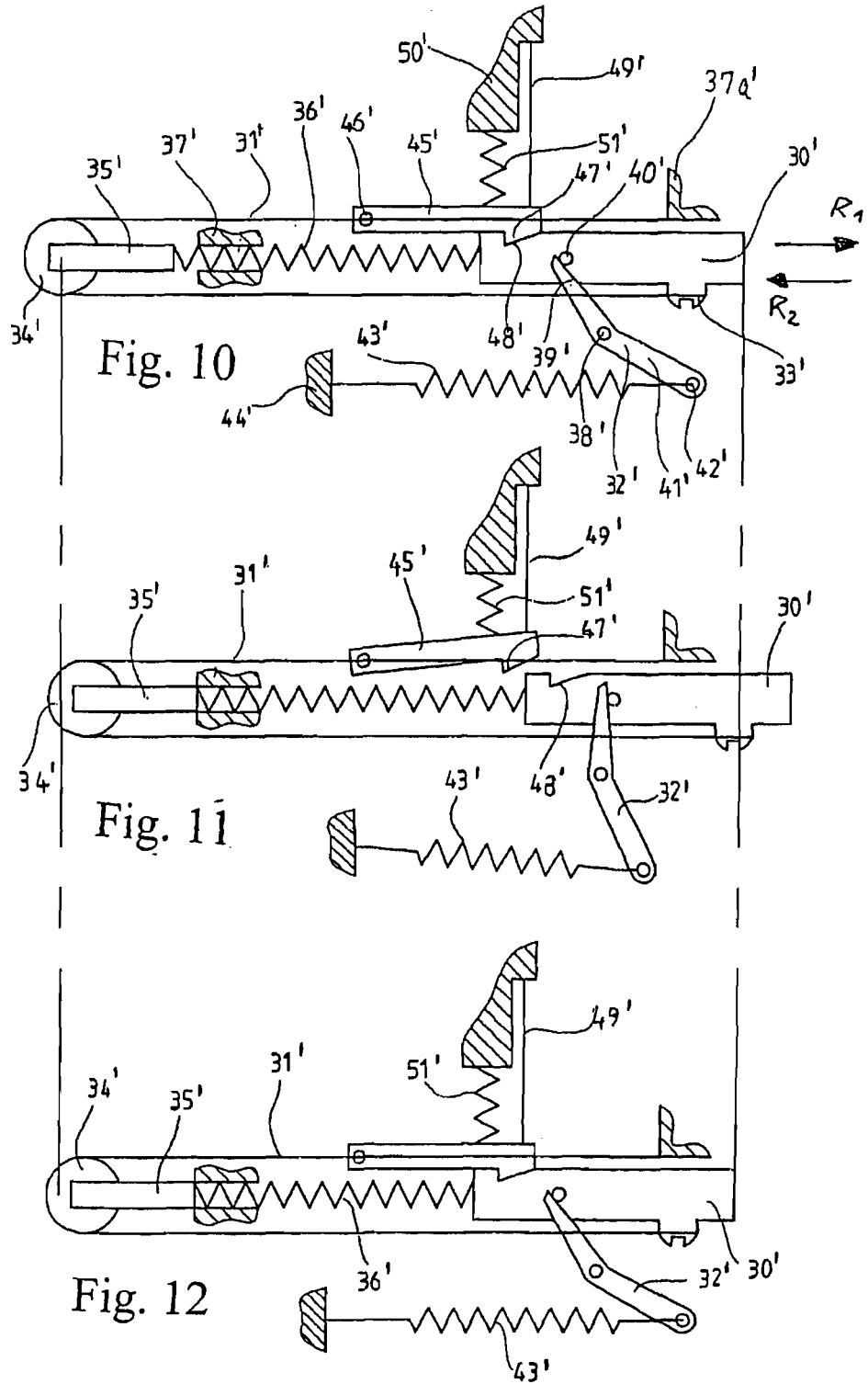

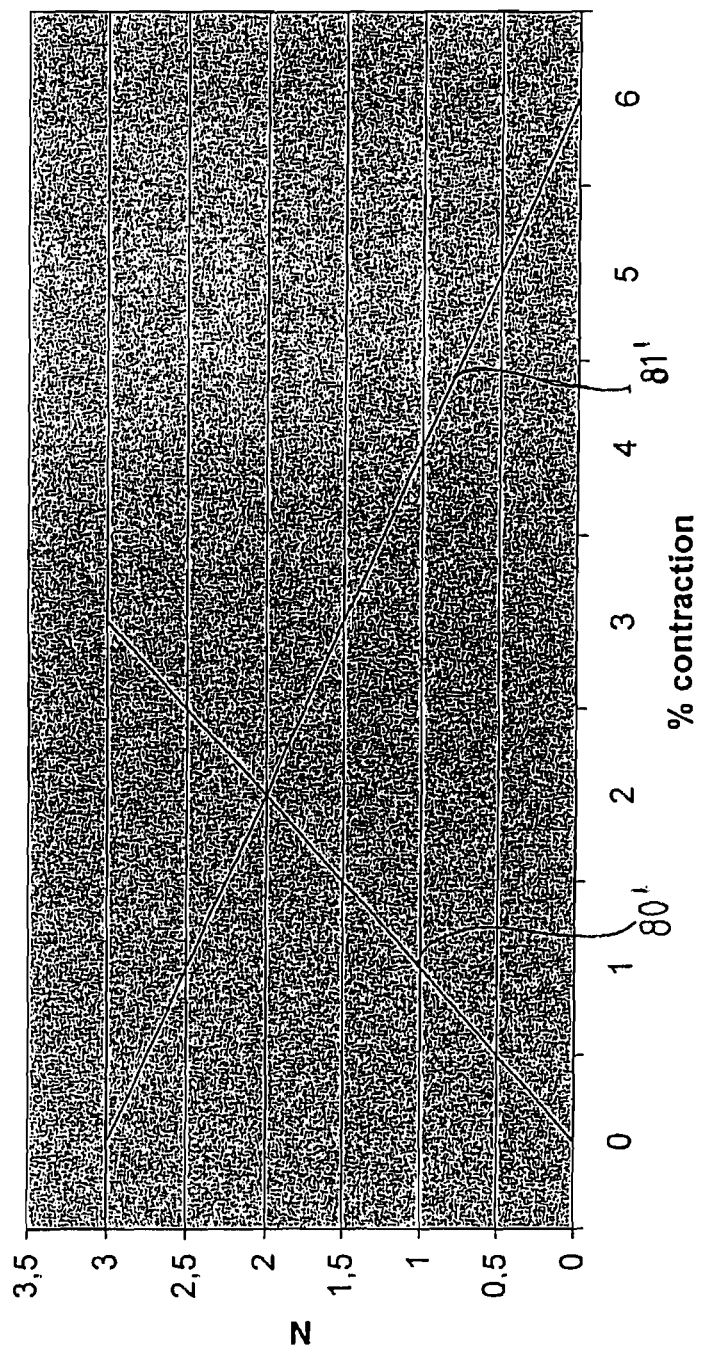

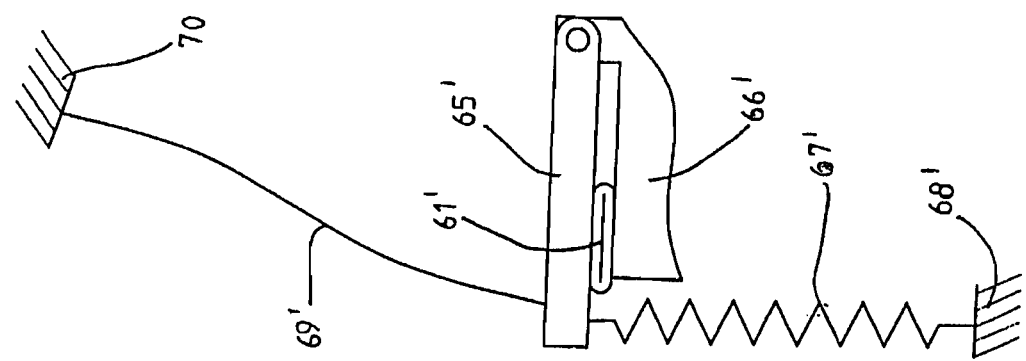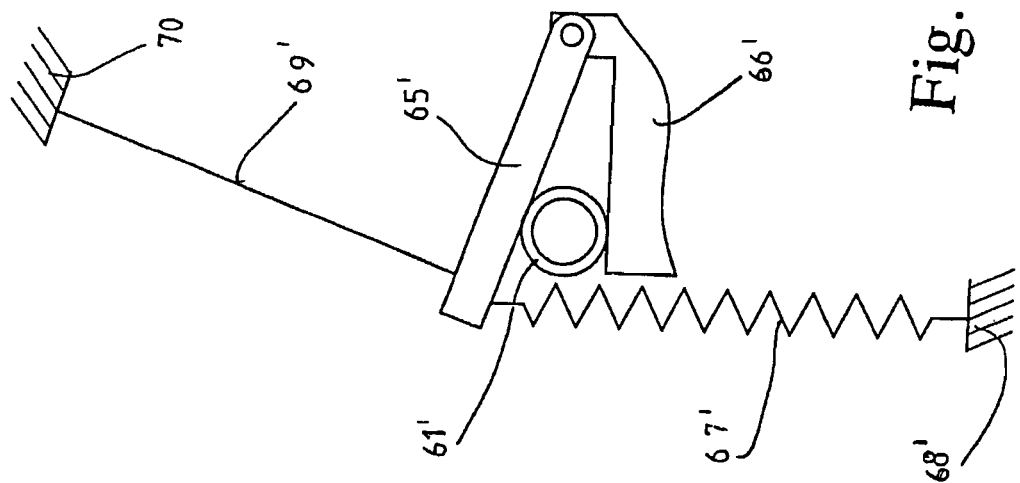
Fig. 18

INFUSION PUMP SYSTEM, AN INFUSION PUMP UNIT AND AN INFUSION PUMP

CROSS-REFERENCE TO RELATED APPLICATIONS

This application is a continuation of U.S. patent application Ser. No. 11/041,189 filed on Jan. 21, 2005 by Morten Mernoe, now U.S. Pat. No. 7,242,423, which is a continuation of International Application No. PCT/DK2003/000507 filed Jul. 21, 2003, which claims priority to Denmark Patent Application No. PA200201133 filed on Apr. 24, 2002. The disclosures of these previous applications are incorporated herein by reference.

FEDERALLY SPONSORED RESEARCH OR DEVELOPMENT

Not Applicable

BACKGROUND OF THE INVENTION

The present invention generally relates to the technical field of infusing a liquid to a patient or person by means of an infusion pump, e.g. at a hospital. The present invention also relates to infusion of liquid to an animal. More precisely, the present invention relates to an infusion pump system and an infusion pump unit of a universal applicable structure for infusing a liquid into a patient or person.

At hospitals or nurse houses, it is often necessary to supply medication or body liquids to a person by means of an infusion pump in which instance the medication or the body liquids are infused into the body of the patient or person in question through a catheter which is connected to the blood transportation system of the patient or person, e.g. a vein or a venule. The usual technique of supplying medication by means of an infusion system to a patient or person involves the supply of physiologic liquid to the patient which physiologic volume is supplied at a specific rate and which serves as a diluting liquid as the medication is supplied to the physiologic liquid also at a specific rate such as one or two drops of medication per time period varying from a second or a few seconds to several minutes or even hours. The medication of a patient or person may in some applications involve the supply of the medication directly to the patient or person by means of the infusion pump.

U.S. Pat. No. 6,270,478 discloses an infusion pump system allowing the patient or person using the infusion pump system to shift from a position sitting or lying in a bed and move around without necessitating the substitution or shift of the stationary infusion pump to a portable infusion pump as the infusion pump system constitutes a universally applicable or combined portable and stationary infusion pump system.

An advantage of this known system relates to the fact that the infusion pump system may be used in different pumping modes as the infusion pump system includes several programmes for different operational modes and further preferably includes input means for input of different operational programmes. U.S. Pat. No. 6,270,478 is hereby incorporated herein by reference.

The pump actuator of the infusion pump units of this known system comprises a magnetic core and a solenoid coil. This actuator is rather bulky, noisy and heavy and requires a relatively large input of electrical energy.

SUMMARY

It is an object of the present invention to provide an infusion pump system, an infusion pump unit for said system and an infusion pump in general were the pump actuator is lighter, smaller, quieter and less power consuming.

According to one aspect of the invention this object is achieved by providing a shape memory alloy actuator as the pump actuator, and said shape memory actuator comprises:
  a body arranged displaceable between a first and a second position,
    releasable holding means adapted for holding said body in said first position,
    at least one first and at least one second wire made of a shape memory alloy such as nitinol, said first wire being at one end connected to said body such that shortening of the length of said first wire exerts a force on said body for moving said body from said second to said first position, and
    a biasing means, such as a tension spring, a compression spring, a straight or arcuate flat spring or a piston and cylinder mechanism, arranged and adapted for biasing said body for moving said body from said first to said second position,
  said second wire having one end connected to said holding means such that shortening of the length of said second wire releases said holding means for allowing said biasing means to move said body from said first position to said second position.

According to another aspect this object is obtained by providing a shape memory alloy actuator as the pump actuator, and said shape memory actuator comprises:
  a body arranged displaceable between a first and a second position,
  at least one first wire made of a shape memory alloy such as nitinol, said first wire being at one end connected to said body such that shortening of the length of said first wire exerts a force on said body for moving said body from said second to said first position,
  a biasing means, such as a tension spring, a compression spring, a straight or arcuate flat spring or a piston and cylinder mechanism, and
  a rotatably arranged intermediate member such as a lever or a disc connected to said body and to said biasing means,
  said biasing means being adapted for exerting a rotation force on said intermediate member for rotating said intermediate member around an axis of rotation in a first direction of rotation from a first angular position to a second angular position, said intermediate member being connected to said body such that rotation of said intermediate member in said first direction of rotation displaces said body from said first position to said second position, and
  said biasing means and said intermediate member being arranged and adapted such that the lever or moment arm of said rotation force with respect to said axis of rotation is larger when said intermediate member is in said second angular position than when said intermediate member is in said first angular position such that said lever or moment arm of said rotation force increases when said intermediate member rotates in said first direction of rotation.

According to a yet further aspect of the invention this object is achieved by providing a shape memory alloy actuator as the pump actuator, and said shape memory actuator comprises:
  a body arranged displaceable between a first and a second position,
    at least one first wire made of a shape memory alloy such as nitinol, said first wire being at one end connected to said body such that shortening of the length of said first wire exerts a force on said body for moving said body from said second to said first position, a biasing means, such as a tension spring, a compression spring, a straight or arcuate flat spring or a piston and cylinder mechanism, and a rotatably arranged intermediate member such as a lever or an arm connected to said body at a force transmission point on said body and connected to or integral with said biasing means, said biasing means being adapted for exerting a rotation force on said intermediate member for rotating said intermediate member around an axis of rotation in a first direction of rotation from a first angular position to a second angular position, said intermediate member being connected to said body such that rotation of said intermediate member in said first direction of rotation displaces said body in from said first position to said second position, and said intermediate member and said body being arranged and adapted such that said rotation force is transmitted to said body as a displacement force applied at said force transmission point for moving said body from said first to said second position, and such that the lever or moment arm of said displacement force with respect to said axis of rotation is larger when said intermediate member is in said first angular position than when said intermediate member is in said second angular position such that said lever or moment arm of said displacement force with respect to said axis of rotation Hereby a quiet, light, mechanically efficient and compact infusion pump is obtained.

In a yet further aspect the present invention relates to a fluid pump, preferably for use in an infusion pump system, an infusion pump unit or as an infusion pump, said fluid pump comprising:

a flexible tube connected to a fluid inlet at one end and connected to a fluid exit at the opposite end, at least three flattening bodies for flattening said tube against an abutment element and arranged along the length of said tube, said bodies being arranged displaceable between a first position, wherein said body is pressed against said abutment element with said tube flattened between said body and said abutment element, and a second position spaced so far from said abutment element that said tube at least partly has regained an open configuration, at least one first wire for each flattening body and made of a shape memory alloy, said first wire being at one end connected to said body such that shortening of the length of said first wire exerts a force on said body for moving said body from said first to said second position, and a biasing means, such as a tension spring, a compression spring, a straight or arcuate flat spring or a piston and cylinder mechanism, for each of said flattening bodies and connected to said flattening body such that a biasing force is exerted on said flattening body in a direction from said second position to said first position.

Hereby an exceptionally light, simple and quiet infusion pump is obtained where the elements that are to be replaced for each infusion are relatively inexpensive and easy to replace.

In a yet further aspect the present invention relates to an infusion pump for infusing a fluid or a paste in a patient, preferably a portable infusion pump and preferably for use in infusing insulin or a pain killer fluid in a patient, said infusion pump comprising:

a housing, a cartridge, ampoule or syringe containing said fluid or paste and removably arranged in said housing and having an outlet aperture and a piston element slidably arranged inside said syringe such that said piston is displaceable towards said outlet aperture, a spindle connected to said piston element and arranged such that rotation of said spindle in a first rotational direction displaces said piston towards said outlet aperture a shape memory alloy actuator incorporated in a shape memory alloy motor comprising:

said shape memory alloy actuator having:

a body arranged displaceable between a first and a second position, at least one first wire made of a shape memory alloy such as nitinol, said first wire being at one end connected to said body such that shortening of the length of said first wire exerts a first displacement force on said body for moving said body from said second to said first position, a biasing means, such as a tension spring, a compression spring, a straight or arcuate flat spring or a piston and cylinder mechanism arranged and adapted for exerting a second displacement force on said body for moving said body from said first to said second position, and a gear having a first and second rotation direction, said body having a portion adapted to fit between two adjacent teeth of said gear, and said body and said gear being adapted and arranged such that in said first position said portion is located between a pair of teeth of said gear and in said second position said portion is located between the adjacent pair of teeth of said gear reckoned in said second rotation direction of said gear such that said second displacement force will cause said body to rotate said gear in said first direction, and said gear being connected to said spindle, preferably via at least one further gear such that rotation of said gear in said first direction causes said spindle to rotate in said first rotational direction.

In a yet further aspect the present invention relates to an infusion pump for infusing a fluid or a paste in a patient, preferably a portable infusion pump and preferably for use in infusing insulin or a pain killer fluid in a patient, said infusion pump comprising:

a housing, a cartridge, ampoule or syringe containing said fluid or paste and removably arranged in said housing and having an outlet aperture and a piston element slidably arranged inside said syringe such that said piston is displaceable towards said outlet aperture, said shape memory alloy actuator, having a body arranged displaceable between a first and a second position, at least one first wire made of a shape memory alloy such as nitinol, said first wire being at one end connected to said body such that shortening of the length of said first wire exerts a first displacement force on said body for moving said body from said second to said first position, a biasing means, such as a tension spring, a compression spring, a straight or arcuate flat spring or a piston and cylinder mechanism arranged and adapted for exerting a second displacement force on said body for moving said body from said first to said second position, and
  a rack having a first and second displacement direction and abutting said piston such that displacement of said rack in said second displacement direction displaces said piston towards said outlet aperture,
said body having a portion adapted to fit between two adjacent teeth of said rack, and said body and said rack being adapted and arranged such that in said first position said portion is located between a pair of teeth of said rack and in said second position said portion is located between the adjacent pair of teeth of said gear reckoned in said second displacement direction of said rack such that said second displacement force will cause said body to displace said rack in said first direction.

In a final aspect the present invention relates to an infusion pump system, comprising:
  at least one infusion pump unit, comprising:
    a housing of a size allowing said infusion pump unit to be carried by a user as a portable infusion pump unit, said housing defining an exterior surface,
    a fluid inlet provided accessibly at said exterior surface for establishing fluid communication from an external infusion bag to said fluid inlet,
    a fluid outlet provided accessibly at said exterior surface for establishing fluid communication to an infusion site,
    a controllable pumping system included within said housing and having an inlet and an outlet, said inlet being connected to said fluid inlet and said outlet being connected to said fluid outlet for allowing transfer of fluid from said fluid inlet to said fluid outlet through activating said controllable pumping system,
    an electronic control means received within said housing for controlling the operation of said controllable pumping system, said electronic control means including at least two preset pumping programs for allowing said controllable pumping system to be controlled in at least two alternative infusion pumping operations, and
    a power supply unit housed within said housing for supplying power to said controllable pumping system and to said electronic control means and connectable through exterior terminals provided at said exterior surface of said housing to external electric energy supply means,
  a stationary receptor system including:
    at least one receptor means for receiving and fixating one of said infusion pump unit therein so as to maintain said infusion pump unit in a stationary mode and exposing said fluid inlet and fluid outlet of said infusion pump unit for allowing access thereto and having first terminals connectable to said exterior terminals for supplying said electric energy to said power supply unit of said at least one infusion pump unit and further having second terminals connectable to third terminals of a second receptor means for supplying power to said second receptor means,
    a mains supply unit for receiving electric energy from the mains supply and having second terminals connectable to said third terminals for supplying said electric energy to said receptor means and thereby to said power supply unit of said at least one infusion pump unit, said mains supply unit constituting said external electric supply means, and
    fastening means for fastening said receptor means adjacent one another and for fastening said mains supply unit adjacent one of said receptor means.

In the currently preferred embodiment, said system further comprises a carrier frame for carrying one infusion pump unit and provided with receiving means for receiving said infusion pump unit and preferably with releasable holding means for holding a container of infusion fluid communicating with said fluid inlet of said infusion pump unit, said receptor means and said carrier frame having cooperating connection means for allowing said frame to be connected to said receptor means such that said external terminals are connected to said first terminals.

Hereby a flexible system is obtained where an optional number of receptor means may be arranged adjacent one another and where great flexibility is achieved as to the transport of an infusion pump unit with the corresponding patient.

BRIEF DESCRIPTION OF THE DRAWINGS

In the following the invention will be explained more in detail in connection with various embodiments thereof shown, solely by way of example, in the accompanying drawings in which FIG. 3 is a schematic view of the interior of the first embodiment of the portable infusion pump unit illustrated in FIGS. 1 and 2, disclosing the flow path thereof, FIG. 4 is a schematic view illustrating a possible application of the first embodiment of the portable infusion pump unit illustrated in FIGS. 1, 2 and 3, FIGS. 10-12 are schematic illustrations of three stages in the operation of a fourth embodiment of an actuator according to the invention, FIG. 13 is a graph showing two curves of Contraction versus Force for shape memory alloy wires for different biasing systems for the actuators according to the invention.

DETAILED DESCRIPTION

Figure 1:
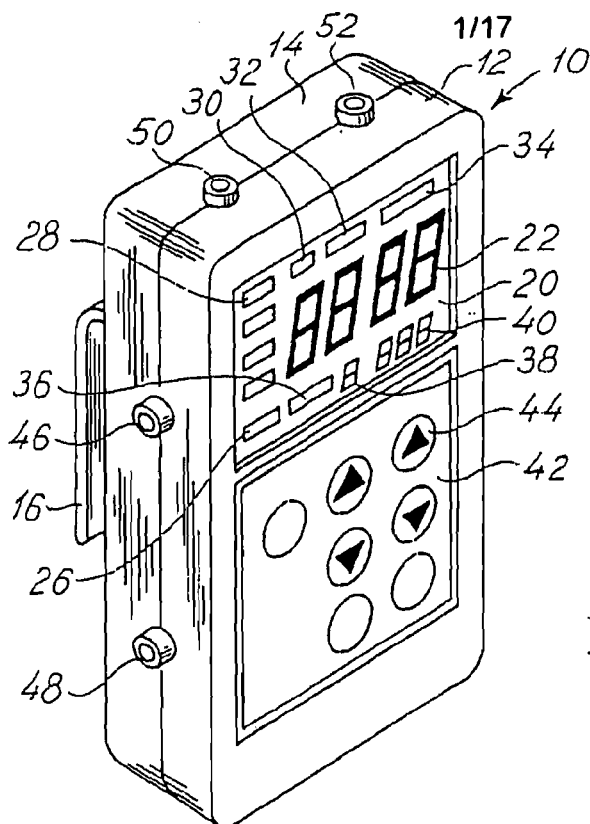
FIG. 1 is a perspective and schematic view of a first embodiment of a portable infusion pump unit according to the present invention.

In the drawings, a first embodiment of a portable infusion pump unit or apparatus is disclosed designated the reference numeral 10 in its entirety. The apparatus 10 comprises a housing composed of two shell-like housing parts 12 and 14 constituting a front and rear housing part, respectively. The front an rear housing parts 12 and 14, respectively, are easily disassembled allowing the user to obtain access to the interior of the apparatus for substituting an interior fluid passage component to be described in greater detail below with reference to FIG. 3 constituting a disposable pre-sterilized component which is easily demounted after use and readily replaced prior to use. From the rear side of the housing part 14, a clip 16 allowing the apparatus 10 to be fixed to a strap or a belt extends. It is to be realised that terms such as upper, lower, front, rear, etc., unless otherwise stated, in the present context define positions or orientations determined by the intentional application of the apparatus 10 as the apparatus is positioned in an upright and substantially vertical position, e.g. received in the belt of a user by means of the clip 16 or otherwise positioned exteriorly or non-implantatedly relative to the user.

In the front housing part 12, a display 20 is provided, comprising two sets of two digits designated the reference numerals 22 and 24, respectively, for displaying digits representing the time lapsed or the time remaining for infusion operation expressed in minutes and hours, respectively, or seconds and minutes, respectively, or alternatively for displaying digits representing the supply of infusion liquid as expressed in volume per time unit, e.g. ml per hour. The display 20 further includes a display area 26 for informing the user and/or a person operating the infusion pump apparatus 10 or nursing the user regarding the operational mode of the apparatus, such as standby or running information. Furthermore, the display 20 includes a number of individual displays positioned above one another and above the standby/running display 26, one of which is designated the reference numeral 28. These individual displays 28 are adapted to display information such as the operational mode, e.g. the information that the apparatus is in a program mode, information regarding whatever information is presented on the two-digit displays 22, 24, such as the time remaining for infusion operation, the total time of the infusion operation, whether or not the apparatus is running or is to be started, or any other relevant information to be presented to the user or operator. The display 20 further includes three individual alarm displays 30, 32 and 34 for informing the user of the presence of air in the infusion pump circuitry, pressure fault or failure or low battery, respectively. A further display 36 informs the user or operator of the program sequence presently used or programmed, which program sequence is represented by a digit displaced by a 1-digit display 38. A 3-digit display 40 of the display 20 represents information to the user or operator regarding the infusion supply measured in ml per hour or similar relevant measure or ratio.

Below the display 20, a keyboard 42 is provided including a set of keys, one of which is designated the reference numeral 44 for allowing the user/operator to control the portable infusion pump unit 10 to perform a specific operation or to program the apparatus by shifting between specific program sequences by increasing a specific digit displayed in a 1-, 2- or 3-digit display, such as the displays 22, 24, 38 and 40, by increasing or reducing the digit in question and by shifting a cursor route relative to the various individual displays of the display 20 for allowing the user/operator to modify the operational mode or shift between various preset programs of the apparatus.

At the one side wall of the housing, composed by the housing parts 12 and 14 of the unit or apparatus 10, two terminals 46 and 48 are provided for allowing the apparatus 10 to be connected to an electronic charger for supplying electric power to an internal rechargeable battery pack or cell of the apparatus. The terminals 46 and 48 may alternatively or additionally serve as input/output terminals for establishing communication between the apparatus 10 and an external apparatus or equipment such as an external data logging apparatus or surveillance apparatus or further alternatively for communicating with an external processing unit such as a personal computer or data logging apparatus. Still further, the apparatus 10 may be provided with a conventional input/output terminal such as a conventional RS 232 terminal for establishing communication between the apparatus 10 and an external computer such as the above-mentioned personal computer for processing data produced by the apparatus concerning the operational mode of the apparatus and also supplementary data produced by the apparatus or auxiliary equipment, e.g. data representing the temperature of the infusion liquid supplied by the apparatus 10 or data supplied by additional external measuring or surveillance equipment. In the top wall of the housing of the apparatus 10 two recesses are provided for receiving two tube connectors 50 and 52 constituting a fluid inlet and a fluid outlet, respectively, of the above-mentioned fluid passage component to be described in further detail below with reference to FIG. 3. As is evident from FIG. 2, a further fluid outlet 54 is provided in the bottom wall of the housing of the apparatus 10 opposite to the fluid outlet 52.

Figure 2:
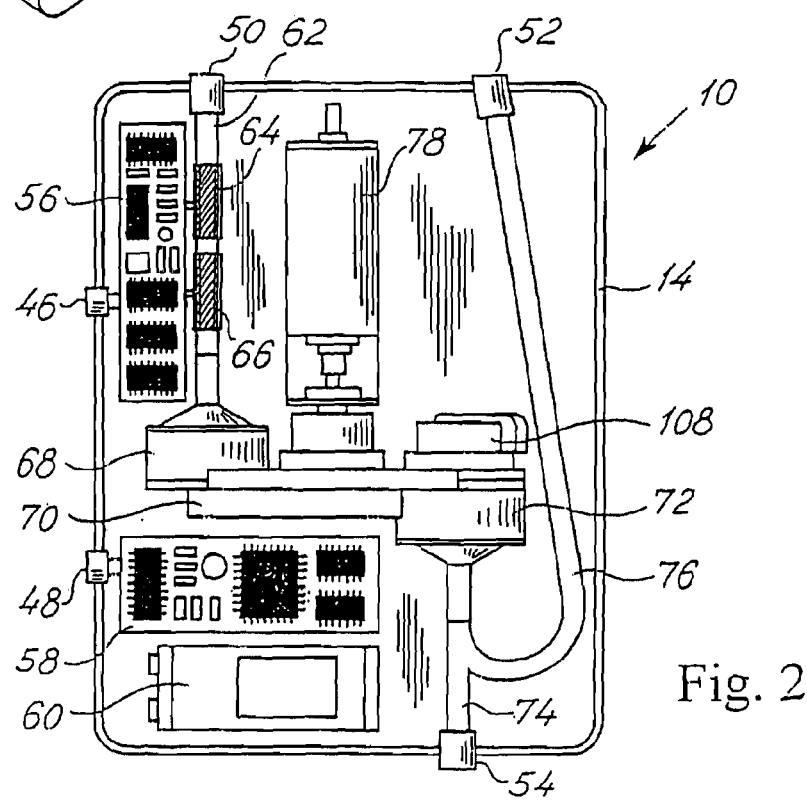
FIG. 2 is an elevational and partly sectional view of the first embodiment of the portable infusion pump unit illustrated in FIG. 1.

In FIG. 2, the interior structure of the portable infusion pump unit or apparatus 10 is disclosed, illustrating the fluid inlet 50 and the fluid outlets 52 and 54. In FIG. 2, the reference numerals 56 and 58 designate two printed circuit boards including the electronic circuitry of the apparatus and including the display, the rechargeable power pack or cell circuitry and the CPU-circuitry of the apparatus controlling the overall operation of the apparatus including the infusion operation. Alternatively, the electronic circuitry of the apparatus may be included in a single printed circuit board or, alternatively, three or more printed circuit boards. The internal re-chargeable battery pack or cell is designated the reference numeral 60.

In FIG. 2, the internal flow system of the portable infusion pump apparatus 10 is disclosed, constituting a disposable and replaceable fluid passage component as mentioned above and including an inlet tube 62 connected to the fluid inlet 50. Two capacitive detectors 64 and 66 are mounted on the inlet tube 62 and communicate with the electronic circuitry of the apparatus housed on the printed circuit board 56 and 58 for detecting presence of air bubbles, if any, in the infusion liquid input to the fluid inlet 50. At its output end, the inlet tube 62 communicates with a first check valve 68 which constitutes an inlet to a pump housing component 70, in which an internal fluid passage is provided, as will be described in greater details below with reference to FIG. 3, which fluid passage terminates in an output or second check valve 72 from which two branched-off outlet tubes 74 and 76 communicate with the fluid outlets 54 and 52, respectively. For transferring the infusion liquid or any other liquid input to the portable infusion pump unit 10 through the fluid inlet 50 to an application site through one of the fluid outlets 52 and 54, a piston type pump actuator 78 is provided. The internal flow system of the portable infusion pump comprising the fluid inlet 50, the inlet tube 52, the capacitive detectors 64 and 66 belonging to the inlet tube 62, the first check valve 68, the pump housing component 70, the output check valve 72, the outlet tubes 74 and 76, and the outlets 52 and 54 constitute an integral disposable and replaceable fluid passage component to be described in greater detail below with reference to FIG. 3.

In FIG. 3, the interior of the check valves and also the pump housing component 70 is disclosed in greater detail. The first check valve 58 basically comprises a central circular cylindrical housing component 80 from which a frusto-conical top part 81 extends upwardly communicating with the inlet tube 62 and arresting an inlet filter element 82 at the transition between the frusto-conical top part 81 and the cylindrical housing component 80. The cylindrical housing component 80 comprises a central annular oral component 84 which is sealed off in the initial or non-active position by a downwardly deflectable sealing membrane 86. Provided the pressure below the sealing membrane 86 is lower than the pressure above the membrane 86, the membrane 86 is forced downwardly allowing liquid to pass through the central aperture of the central annular component 84 and further through apertures 87 provided offset relatively to the centre of the sealing membrane 86.

The first check valve 68 communicates with an inlet passage 88 of the pumping house component 70 terminating in an inner chamber defined within an upwardly protruding annular top housing component 90 in which a reciprocating plunger 94 of the piston pump actuator 78 is movable in the direction to and from an abutting pin 96 which separates the inlet passage 88 from an outlet passage 98. The interspace between the reciprocating plunger of the piston pump 78 and the inner surface of the annular top housing component 90 is sealed by means of a highly flexible sealing gasket 92.

The outlet passage 98 communicates with the above described second check valve 72 which is basically of a configuration similar to and functioning as a check valve similar to the above described first check valve 58, however differing from the above described first check valve in that the second check valve 72 does not include any filter element similar to the filter element 82. The second check valve 72 includes a downwardly protruding annular housing part 100, which is cast integral with the pumping house component 70, fulfilling, however, the same purpose as the above described annular housing part 80 of the first check valve. From the annular housing part 100, a downwardly protruding frusto-conical housing part 101 similar to the above described frusto-conical housing part 81 extends communicating with the outlet tube 74 and similarly the outlet tube 76 described above with reference to FIG. 2. Within the annular housing part 100, a sealing membrane 102 similar to the above described sealing member 86 is received, which includes apertures 103 similar to the apertures 87 described above. The sealing membrane 102 communicates with a conical bore 99 communicating with the outlet passage 98 for sealing off communication from the outlet passage 98, through the conical bore 99 to the outlet tube 74 provided the sealing membrane 102 rests against an abutting lower surface defining the lower boundary of the conical bore 99.

The pumping operation of the portable infusion pump unit 10 is established as follows. Initially, the first check valve 68 and the second check valve 72 are in their initial and sealing positions. It is also assumed that liquid is present within the inlet tube 62 within the inlet passage 88 and the outlet passage 98 and also within the outlet tube 74. The piston pump actuator 78 is activated through the supply of an electric signal such as an alternating electric signal or a pulsed signal causing the reciprocating plunger 94 to move upwardly or downwardly. The piston pump actuator 78 will be described in greater detail below with reference to FIGS. 6-12. The plunger 94 is pressed downwardly in relation to the orientation of the piston pump actuator 78 shown in FIG. 3.

Assuming that the first movement of the reciprocating plunger 94 is in movement upwardly, a relative vacuum is created within the inlet passage 88 and the outlet passage 98 by the increase of the volume defined below the sealing gasket 92. Through the creation of the relative vacuum within the inlet passage 88, the first check valve 68 is operated as the downwardly deflectable sealing membrane 86 is caused to move downwardly allowing liquid to flow into the inlet channel 88 through the central aperture of the central annular component 84 as described above. At the same time, the relative vacuum within the outlet passage 98 creates a relative vacuum above the sealing membrane 102 which is biased so as to prevent free flow through the second check valve 72 urging or forcing the sealing membrane into sealing off and abutting engagement with a wall part circumferentially encircling and defining the conical bore 99, and consequently preventing liquid from being transferred from the outlet passage 98 to the outlet tube 74. In summary, during the raising of the reciprocating plunger 94, the first check valve 68 is activated and caused to open whereas the second check valve 72 is blocked.

As the reciprocating plunger is moved downwardly, a relative increased pressure is created within the inlet passage 88 and the outlet passage 98 and the operations of the first and second check valves are shifted as the relative increased pressure within the inlet passage 88 causes the first check valve 68 to block and seal off whereas the increased pressure within the outlet passage 98 causes the second check valve 72 to open allowing the fluid present within the outlet passage 98 to be forced out through the conical passage 99, through the apertures 103 of the sealing membrane 102 and further into the outlet tube 74. The rate of transfer and consequence the flow of liquid from the outlet tube 74 is controlled by the rate of operation of the piston pump actuator 78 as an increased frequency of reciprocating the reciprocating plunger 94 increases the velocity of flow of fluid or liquid from the inlet tube 62 to the outlet tube 74.

Above the second check valve 72, a bypass valve is provided, comprising a sealing membrane 104 which is acted upon by a central stem element 106 of a turnable knob 108 so as to force the sealing membrane 104 into sealing off and abutting engagement with a conical bore 105 provided above and in registration with the above described conical bore 99. Provided the conical bore 105 is sealed off by means of the sealing membrane 104, the bypass valve is not in operation. Provided the sealing membrane 104 is raised from its sealing off and abutting engagement with the conical bore 105 as the knob 108 is rotated for causing elevation of the actuator stem 106, communication from the outlet passage 98 is established through a bypass passage 110, bypassing the communication from the outlet passage 98 through the conical passage 99 for allowing fluid to flow from the outlet passage 98 through the bypass passage 110 and further through the apertures 103 of the sealing membrane 102 which is consequently not functioning as the bypass valve is in operation.

The piston pump actuator 78, which may constitute a replaceable component of the portable infusion pump unit or apparatus 10, may provide a specific stroke and, consequently, a specific flow volume per stroke. Therefore, the actuator 78 is preferably provided with a switch cooperating with a switch of the electronic circuitry of the apparatus for informing the microprocessor of the electronic circuitry of the apparatus of the type of piston pump actuator included within the apparatus at present. The technique of providing information to the microprocessor concerning the type of piston pump included within the apparatus at present may be established by means of numerous techniques well-known in the art per se such as by means of code switches, optic capacitive or inductive readers, or simply by means of a feedback circuit monitoring the work rate of the piston pump actuator.

In FIG. 3, an inlet tube 112 is shown establishing communication from the inlet tube 62 through the fluid inlet 50 not shown in FIG. 3, however, shown in FIG. 2 from an infusion bag 114 which may constitute an infusion bag including an infusion liquid simply constituting physiological liquid or additionally or alternatively a drug suspended in any appropriate liquid, or alternatively blood plasma. The outlet from the outlet tube 74 of the portable infusion pump unit 10 shown in FIG. 4 is connected to an outlet tube 116 through the fluid outlet 54, not shown in FIG. 3, however, shown in FIG. 2, which external outlet tube 116 communicates with a cannular assembly 118 of a basically conventional structure.

The inlet tube 112 and the outlet tube 116 may constitute separate inlet and outlet tubes to be connected to the infusion pump unit 10 through the inlet and outlet 50 and 52 or, alternatively, 54, respectively. Alternatively, and preferably, the inlet tube 112 and the outlet tube 116 constitute integral components of the disposable and replaceable fluid passage component illustrated in FIG. 3, which fluid passage component is cooperating with and activated by means of the piston pump actuator 78. Further alternatively, the infusion bag 114 may be configured and housed within a container component which is configured so as to allow the infusion bag 114 to be received and supported on top of the infusion pump unit or apparatus 10 as the above-mentioned receiver is simply connected to and supported by the housing of the portable infusion unit or apparatus 10.

The infusion of liquid from the infusion bag 104 is further illustrated in FIG. 4, in which the portable infusion pump 10 is received and fixed relative to an individual 120 by means of a belt or strap 122 on which the infusion bag 114 is further fixated. In FIG. 4, the external inlet tube 112, the external outlet tube 116 and the cannular assembly 118 are also illustrated.

Figure 5:
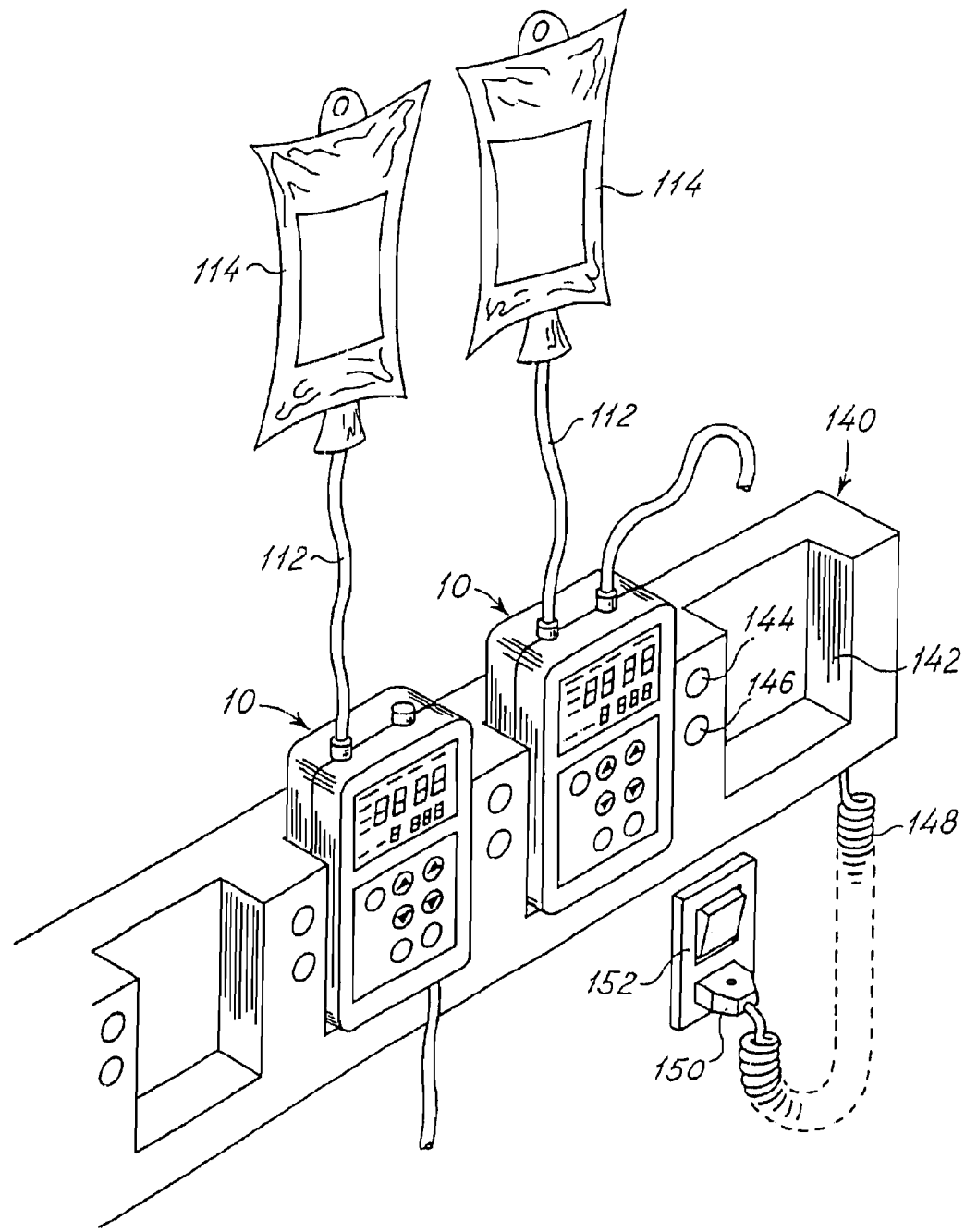
FIG. 5 is a perspective and schematic view illustrating the application of the first embodiment of the portable infusion pump unit illustrated in FIGS. 1-4 in a stationary charger and fixation system for providing a stationary infusion pump system.

In FIG. 5, the above described first embodiment of the portable infusion pump unit or apparatus 10 is shown in duplicate received within a stationary receptor 140 in which a plurality of receptor compartments 142 are defined. Each of the receptor compartments 142 is provided with a set of charger terminals for establishing electrical conductive communication with the charger terminal 46 and 48 of the apparatus or unit 10 received within the receptor compartment 140 in question for charging the internal rechargeable battery pack or cell of the apparatus or unit through the supply of electric energy from a mains power supply unit of the receptor assembly 140 which mains supply power supply unit receives electric power through a coiled mains supply wire 148 terminating in a mains plug 150 which is received in a mains AC outlet socket 152.

The receptor assembly 140 further includes a set of indicator lamps 144 and 146. Provided none of the indicator lamps 144 and 146 corresponding to a specific receptor compartment 142 are turned off, the indication informs the user or operator that no charging is taking place in the receptor compartment in question. Provided a portable infusion pump unit is received within a specific receptor compartment 142, one of the lamps 144 and 146 corresponding to the receptor compartment is turned off, one of which informs the user or operator that the potable infusion pump unit in question is to be recharged, or alternatively the other lamp is turned on informing the user or operator that the portable infusion pump unit in question is fully charged and ready for use. Alternative information display modes, such as flashing of lamps for informing malfunction in the rechargeable battery pack or cell of the portable infusion pump is of course also readily deduceable.

In connection with infusion pumps, particularly portable medicinal infusion pumps, it is important that the pumping action be carried out by a very compact actuator functioning as quietly as possible, with as low energy consumption as possible and with as small a waste heat production as possible.

The pump actuator 78 in FIGS. 2 and 3 is, according to the invention, a shape memory alloy actuator which embodies all the above desirable characteristics. Several shape memory alloy actuators for use as a pump actuator in medicinal infusion pumps will be described in following, it being understood that these actuators are particularly useful as the pump actuator 78 in FIGS. 2 and 3.

Figure 6:
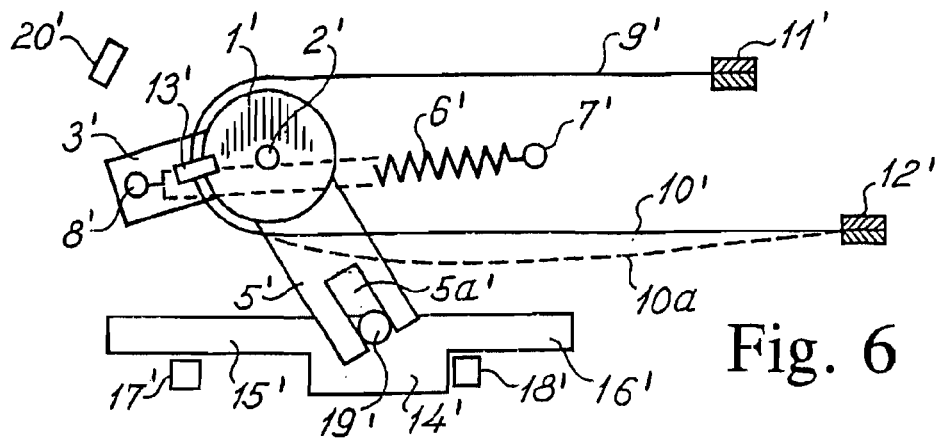
FIGS. 6 and 7 are schematic illustrations of a first embodiment of a pump actuator according to the invention in two different positions, namely with the activating pin fully retracted in FIG. 6, and with the activating pin fully extended in FIG. 7, FIGS. 8 and 9 are schematic illustrations of a second and third embodiment, respectively, of a pump actuator according to the invention.
Figure 7:
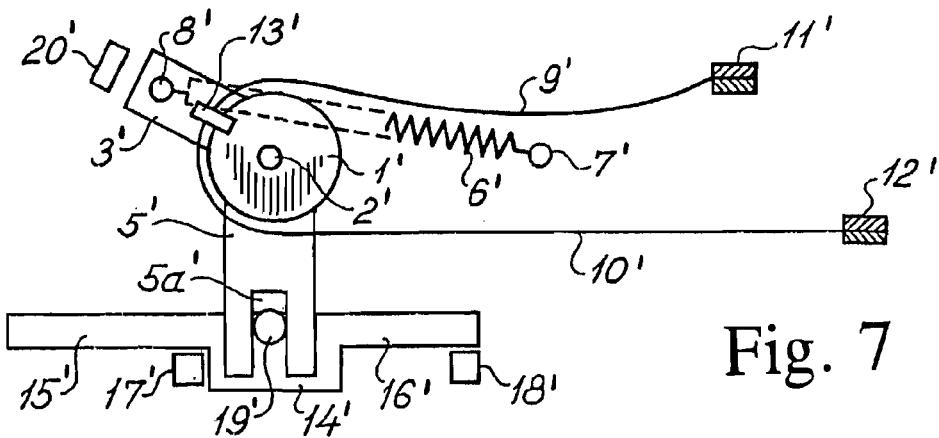

Referring now to FIGS. 6 and 7, a pivotable body in the form of a circular disc 1' is arranged for pivoting around a central pivot 2' fixedly attached to a not shown frame of the actuator, and the disc 1' is provided with a peripheral extension 3' and a yoke-like peripheral extension 5'. A tension coil spring 6' is at one end thereof pivotably attached to a fastening pin 7' fixedly attached to said frame and is at the other end thereof pivotably attached to a fastening pin 8' fixedly attached to the peripheral extension 3'.

Two wires or filaments 9' and 10' of a shape memory alloy such as nickel titanium alloy or nitinol, for instance supplied by the company DYNALLOY, INC, of Costa Mesa, Calif., USA, under the trade name FLEXINOL, are attached at one end thereof to electrically conductive terminals 11' and 12', respectively, fixedly attached to said frame.

The other end of each of the wires 9' and 10 is attached to an electrically conductive terminal 13' fixedly attached to the periphery of the disc 1'. The wires 9' and 10' extend along the periphery of the disc 1' such that the wires 9' and 10' when tensioned extend along and are supported by said periphery. In the drawings the wires 9' and 10' are shown spaced from said periphery for the sake of clarity.

A sliding body 14' having two arms 15' and 16' is arranged for sliding movement between two stop pins 17' and 18' attached to the frame. A pin 19' attached to the sliding body 14' is received in the fork 5a' of the yoke-like extension 5' such that the pin 19' may slide and rotate freely in the fork when the disc 1' pivots from the position shown in FIG. 6 to the position shown in FIG. 7 thereby slidingly displacing the body 14' from abutment against stop pin 18' to abutment against stop pin 17' with the arm 15', constituting the activating pin of the actuator, fully extended.

A proximity sensor 20' is attached to the frame and connected to not shown electrical conductors for transmitting a signal from the sensor to a not shown receiver. The terminals 11' and 12' are likewise each connected to an electrical conductor, not shown, connected to a not shown power source for supplying electrical power to the wires 9' and 10' for resistance heating thereof, the terminal 13' being likewise connected to the not shown power source through a not shown electrical conductor for closing the resistance heating circuit.

In use, the wires 9' and 10' are intermittently heated to the transformation or transition temperature (from martensitic to austenitic state) of the shape memory alloy which temperature for nitinol is approximately 90° C. Thereby the length of the wire is shortened. When the wire cools to below 90° C. the length thereof reverts to normal, i.e. the wire lengthens. The speed at which the shortening takes place, i.e. the contraction time, is directly related to the current input. i.e. the voltage applied over the terminals 11' or 12' and 13'.

In the position depicted in FIG. 6, the intermediate disc 1' is in its outermost counter clock-wise position with the arm 15' fully retracted and with the wire 9' cooled to below 90° C. and the wire 10' heated to above 90° C. by applying an electrical voltage between the terminal 12' and 13' whereby an electrical current will flow through the wire 10'. The disc 1' has therefore been rotated counter clock-wise to the position shown by the contraction force exerted by the wire 10'.

In the next step, the wire 10' is cooled to below 90° C. and thereby lengthens to the shape indicated by the dotted line 10a' in FIG. 6. The actuator is now ready to perform an activating extension of the arm 15' towards the left, the end of the arm 15' being intended to come into contact with a not shown plunger 94 and depress or activate same during the movement of the arm 15' to the extended leftwards position thereof as depicted in FIG. 7.

Thereafter or simultaneously, the wire 9' is heated to above 90° C. whereby it contracts and exerts a clock-wise force on the disc 1' pivoting it clock-wise around the pivot 2' past the balance position of the disc 1' and spring 6' in which the attachment pins 7' and 8' of the spring 6' are aligned with the pivot 2'.

When the disc 1' has rotated clock-wise past said balance point, the tension force exerted by the spring 7' will continue the clock-wise rotation of the disc 1' to the position shown in FIG. 7 with the arm 15' fully extended and the wire 9' slack though still above 90° C. This is the actual activating movement of the actuator where the force applied to the sliding body 14' by the extension 5' increases because of the increasing lever of force or moment arm of the tension force exerted by the spring 6' on the intermediate disc 1' with respect to the pivot 2' or axis of rotation of the disc 1'.

Figure 14:
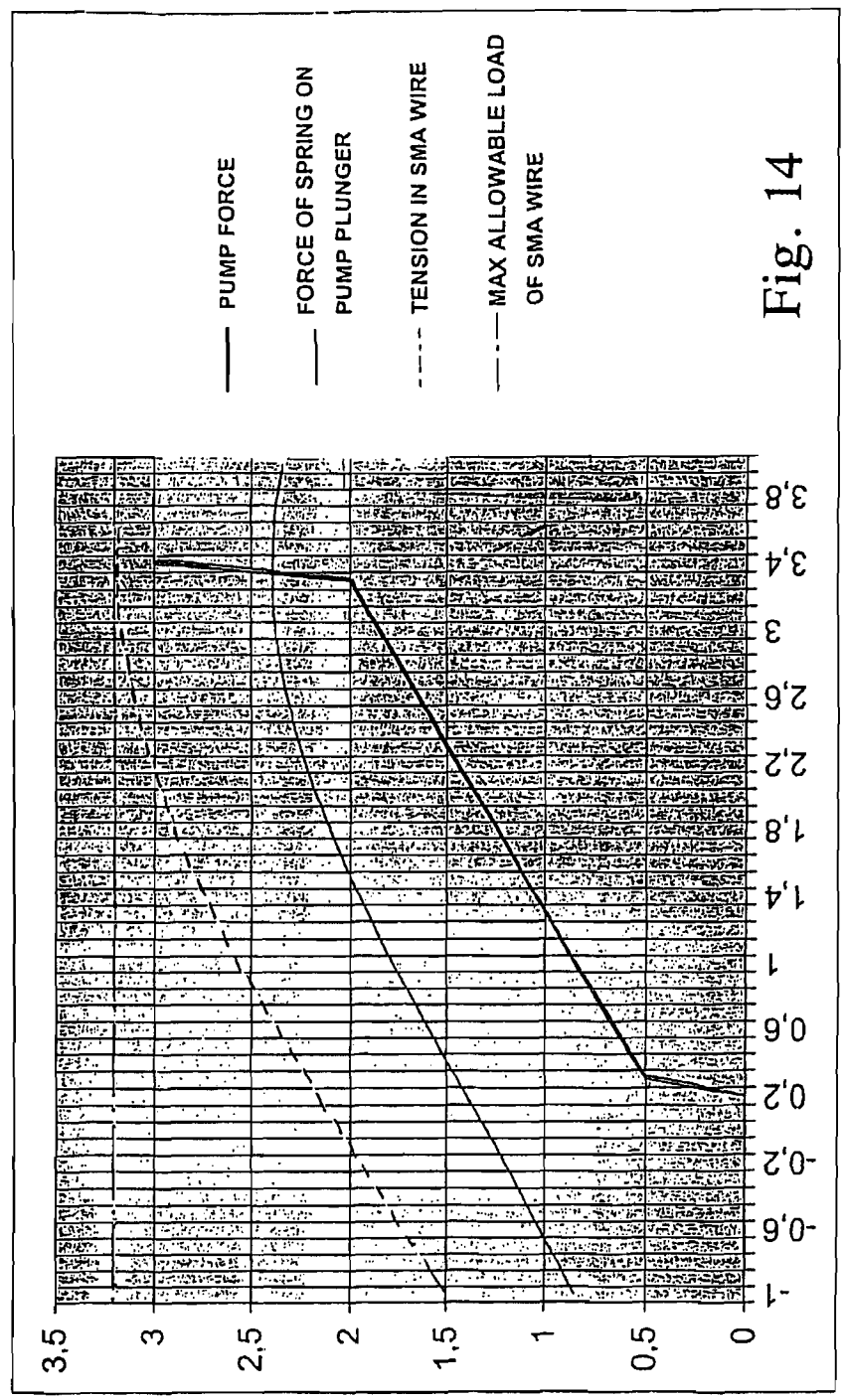
FIG. 14 is a graph showing the relationship between various forces in Newton and the distance of displacement of a piston pump plunger in mm by the actuator shown in FIGS. 10-12.

For applications where the force necessary to perform the function of the actuator, such as depressing the pump plunger 94 in FIG. 3, increases during the activating stroke, said increase of the spring force moment arm as the disc 1' rotates is a very advantageous feature as will be explained more in detail in connection with FIGS. 13 and 14 in the following.

An increase of the activating force of the actuator during the activating stroke is also achieved or enhanced by decreasing the distance of the pin 19' from the pivot 2' or axis of rotation of the disc 1' during the activating stroke whereby the moment arm or lever of force of the displacement force exerted on the pin 19' by the yoke-like extension 5' with respect to the pivot 2' is decreased and thereby the displacement force is increased during the activating stroke. This shortening of said distance can be seen from the situation in FIG. 6 at the beginning of the activation stroke to the situation in FIG. 7 at the end of the activation stroke.

Finally, the wire 10' is heated above 90° C. so that it contracts and pivots the disc 1' back to the position shown in FIG. 6 whereby the activating cycle is ready to be repeated.

The length of the wire 10' is larger than the length of the wire 9' because the contraction or shortening of the wire 10' must be large enough to pivot the disc 1' from the position shown in FIG. 7 past the balance point mentioned above while the shortening of the wire 9' only has to be enough the pivot the disc 1' from the position shown in FIG. 6 past said balance point.

Nitinol wires will typically contract about 3%-6% when heated past the transition temperature. The uncontracted length of the wire 10' should be enough to ensure that the uncontracted wire is fully extended in the position shown in FIG. 7 and that the contracted wire 10' is fully extended when the disc 1' is at least slightly past said balance point in the counter-clockwise direction, i.e. the uncontracted length of wire 10' should be about 22-25 times the distance of travel of terminal 13' between the FIG. 7 position thereof and the balance point position thereof.

The necessary contraction force to be exerted by wires 9' and 10' are rather different because the contraction force of wire 9' only has to counteract the torque or moment of the spring force of spring 6' with the relatively small torque arm in FIG. 6 while the contraction force of wire 10' has to counteract the considerably larger torque of said spring force in FIG. 7. The contraction force of a nitinol wire is larger the larger the diameter or cross sectional area of the wire. The cross sectional area of wire 10' is thus considerably larger than the cross sectional area of wire 9' or there may be a number of wires 10' with the same cross sectional area.

The latter possibility is chosen if it is necessary that the cooling-off time for the wires 10' is as short of possible so that the interval between the activating cycles may be as short as possible. Several small diameter wires with a certain total cross sectional area will cool more rapidly than a single larger diameter wire with the same cross sectional area.

The signal emitted by the proximity sensor 20' each time the extension 3' is in the position shown in FIG. 7 may be utilised for many different purposes such as for instance a mere monitoring of the correct function of the actuator or for controlling the timing of the heating of the wires 9' and 10' and thereby the timing of the activating stroke of the sliding body 14'. Naturally, the location of the proximity sensor or of any other type of sensor for sensing the position of the disc 1' may be varied according to the purpose thereof, and several such sensors may be provided in different locations for instance for achieving a more complex control of the timing of the activating effect of the actuator.

Figure 8:
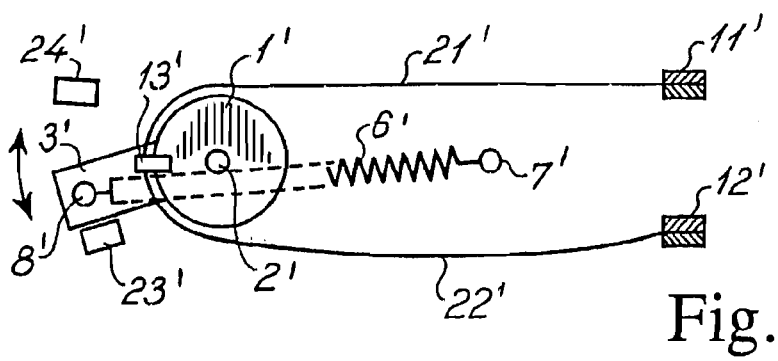

Referring now to FIG. 8, this embodiment differs from the embodiment of FIGS. 6-7 in that a double activating effect may be achieved for each cycle of heating and cooling the shape memory wires 21' and 22' that in this case are of equal length and cross sectional area. The rotation of the disc 1' counter-clockwise and clockwise is limited by stop pins 23' and 24', respectively.

The activating member may be a sliding body similar to body 14' in FIG. 6-7 where both the arm 15' and the arm 16' perform an activating function, or the activating function may be a pull/push activation by for instance arm 15'.

The disc 1' may alternatively be provided with a central torsion shaft projecting at right angles to the plane of the disc 1' as a prolongation of the pivot 2' such that the torsion shaft functions as the activating member by for instance rotating a lever to and fro. Many different types of activating members connected to the disc 1' will be obvious to those skilled in the art.

In the position shown in FIG. 8, the disc 1' has just performed an activating rotation counter-clockwise under the influence of the counter-clockwise torque of the force of the spring 6' and is ready for the initiation of a rotation clockwise by heating the wire 21' so that the disc 1' is rotated against the counter-clockwise torque of the spring force until the balance point is passed. Then the activating rotation clock-wise is performed by the clock-wise torque of the spring force. Also in this embodiment the moment arm of the activating force of the spring 6' increases during the activating stroke in both directions.

Figure 9:
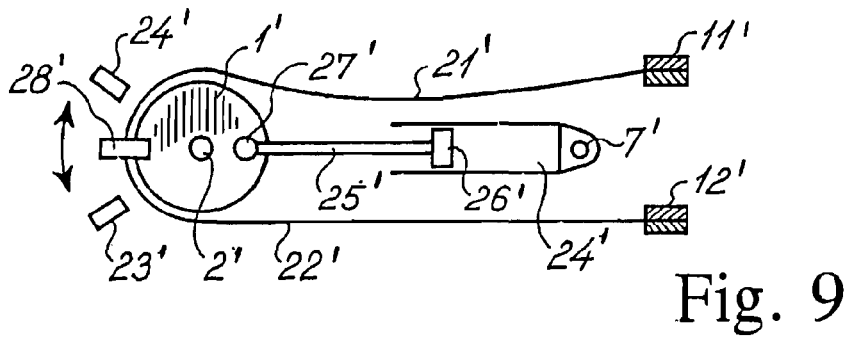

Referring now to FIG. 9, the terminal 13' of the embodiments of FIGS. 6-8 has been substituted by a combined terminal and abutment member 28' for abutting the stop pins 24' and 25'. Furthermore, another type of biasing means is utilized, namely a piston and cylinder mechanism comprising a pressurized cylinder 24' pivotably attached to pin 7', a piston 26' and a piston rod 27' pivotably attached to the disc 1' by means of a pin 27'.

The piston and cylinder mechanism 24'-25' functions like a compression spring and could in fact be substituted by a compression spring. In FIG. 9 the disc 1' is in the balance point position where the pin 7', the pin 27' and the pivot 2' are aligned such that the pressure exerted on the disc 1' by the piston rod 25' does not produce any torque on the disc 1'. In the situation shown in FIG. 9, the wire 22' is contracting and rotating the disc counter clock-wise past the balance point. As soon as the balance point has been passed, the torque from the piston rod 25' will cause the activating counter clock-wise rotation of the disc 1' until the member 28' abuts the stop pin 23' whereupon a clockwise rotation may be initiated in a manner very similar to that described above in relation to FIG. 8.

The tension spring 6' in FIGS. 6-7 could also be substituted by a piston and cylinder mechanism or a compression spring in an arrangement similar to FIG. 9.

Referring now to FIGS. 10-12 an activating body 30' is arranged linearly displaceable in the directions of arrows R1 and R2 under the influence of a shape memory alloy wire 31' and a two-armed lever 32'.

One end of the wire 31' is attached to the body 30' at 33' and the other end is attached to a fixed portion 37a' of a not shown frame of the actuator, the wire 31' extending around a pulley 34' pivotably arranged on a slide 35' displaceable in the directions of the arrows R1 and R2. A compression spring 36' is arranged between the body 30' and the slide 35' and extends through a passage through a fixed portion 37' of said frame.

The two-armed lever 32' is arranged pivotable around a pivot 38', one arm 39' of the lever abutting a pin 40' on the body 30' and the other arm 41' of the lever being attached at 42' to one end of a tension spring 43', the other end being attached to a fixed portion 44' of said frame such that displacement of the body 30' in the direction of arrow R1 tensions the spring 43' via rotation of the intermediate lever 32'.

A pawl or hook element 45' is arranged pivotable around a pivot 46' such that a hook or projection 47' of the hook element 45' may be received in a matching recess 48' in the body 30'. A shape memory alloy wire 49' is at one end attached to the hook element 45' and at the other end attached to a fixed portion 50' of said frame. A compression spring 51' is arranged between the fixed portion 50' and the hook element 45'

In use, the body 30' is moved to and fro in the direction of the arrows R1 and R2 to activate the plunger 94 during the activating stroke of the body in the direction R1.

In FIG. 10 the wire 31' is cooled to below the transformation temperature of the alloy (for instance by sandwiching the wire between two aluminum rails coated with PTFE) and is at its maximum length and is maintained taut by the biasing action of the compression spring 36'. The hook 47' is received in the recess 48' and holds the body 30' against the biasing force of the spring 43' transmitted to the pin 40' by means of the lever 32'. The wire 49' is also in its cool state and at its maximum length.

When the activating stroke is to be initiated, the wire 49' is heated to the transformation temperature and shortens or contracts, thereby pivoting the hook element 45' against the biasing force of the spring 51' such that the hook 47' is pulled out of the recess 48' to the release position shown in FIG. 11. The body 30' is thus released for displacement in direction R1 under the influence of the lever 32' pivoted by the spring 43'.

During the activating stroke of body 30' in direction R1 the lever or moment arm of the force exerted by the spring 43' relative to the pivot 38' or the axis of rotation of the lever 32' increases such that the displacement force exerted on the pin 40' by the arm 39' increases as the body 30' is displaced in the direction R1.

Likewise, during the activating stroke by the body 30' in direction R1, the lever or moment arm of the displacement force exerted by the arm 39' on the pin 40' relative to the pivot 38' decreases whereby said displacement force increases as the body 30' is displaced in the direction R1.

When the slide 35' abuts the fixed frame portion 37', the activating stroke in direction R1 will be stopped as shown in FIG. 11. In practice the activating stroke preferably is stopped by the resistance to the activating stroke of the body 30' by the plunger 94 being activated such that the stroke is stopped before the slide 35' abuts the fixed frame portion 37'.

So as to cock the actuator again, the wire 49' is cooled to allow the spring 51' to pivot the hook element 45' towards the holding position thereof while the wire 31' is heated until it shortens and thereby causes the slide 35' to abut the fixed frame portion 37' and the pulley 34' to rotate clock-wise while the body 30' is displaced in the direction R2 against the force of the spring 43' that thereby is lengthened while the lever 32' pivots counter clock-wise. When the body 30' has reached the position shown in FIG. 12, the hook 47' is pressed into the recess 48' and the wire 31' may then be cooled so that the situation in FIG. 10 is re-established ready to initiate a new activation cycle of the actuator.

During the tensioning of the spring 43', the force exerted by the wire 31' necessary for this tensioning is largest at the beginning of the displacement of the body 30' in the direction R2 because of the large moment arm of the force of the spring 43' and the small moment arm of the rotation force of the pin 40' on the arm 39', and the force exerted by the wire 31' decreases as the body 30' is displaced in the direction R2. This is an advantageous development of the force in the wire 31' during the cocking of the actuator as will be explained more in detail in the following in connection with FIGS. 13 and 14.

By adapting the actuator according to the invention such that the activating stroke is performed by a force exerted by a biasing means, a further advantage is obtained in that any blocking of the activating stroke of the activating body, for instance because the pump plunger 94 is blocked, will only entail that the activation stroke is stopped with no damage to the SMA wire. If the activating stroke were carried out under the influence of a shortening of a shape memory alloy wire, said wire would probably be damaged or snapped if the activating stroke were blocked.

The extra length of the wire 31' obtained by means of the pulley 34' is advantageous for giving a longer activating stroke with a compact construction of the actuator.

The heating of the wires 31' and 49' is carried out in a manner similar to the heating of the wires 9' and 10' in FIGS. 6-7 by means of not shown electrically conductive connections of the ends thereof to the battery pack 60 of the infusion pump unit according to the invention.

Referring now to FIG. 13, the curve or line 80' indicates the relationship between the force exerted by an SMA wire on a body in one direction while the body id biased by a tension spring in the opposite direction as a function of the contraction or shortening thereof. The force increases proportionally with the contraction because of the proportional increase of the spring force of the spring when it is stretched by contraction of the wire.

The line or curve 81 is symbolic of the curves corresponding to the relationship between contraction and force exerted for the embodiments of FIGS. 6-9 where the force in the wires 10', 22', 24' and 31', respectively is largest at the beginning of the contraction or shortening, and the contraction length of the wire is much larger because of the variation in the length of the moment arm or arms during the activating stroke as described above.

In this manner, a high coefficient of mechanical efficiency is obtained because the longer contraction distance for a given input of energy to heat the SMA wires gives an increased input of energy into the activating system.

The actual curves 81 will not be linear but will reflect the varying rate of change of the moment arm or moment arms during the activating stroke.

Referring now to FIG. 14 and FIGS. 10-12, an actuator as shown in FIGS. 10-12 is applied to depress the plunger 94 of the infusion pump in FIG. 3 thereof with the body 30'.

The plunger 94 and body 30' travel from 0.2 mm to 3.4 mm during the activating stroke of the body 30'. The force required to displace the plunger increases substantially proportionally from approx. 0.5 N to approx. 2N where the force increases steeply because the plunger has reached the end of its path.

The force exerted by the spring 43' on the body 30' and thus the plunger 94 develops as an increasing parable-like curve corresponding to the curve for the tension or force in the SMA wire 31' necessary to retract the body 30' against the leveraged force of the spring 43'.

It is clear that the curves show that the actuator according to the invention can produce an increasing force as the displacement increases which is very advantageous in applications such as pumping with piston pumps where the force required increases with the distance traveled by the plunger.

Figure 15:
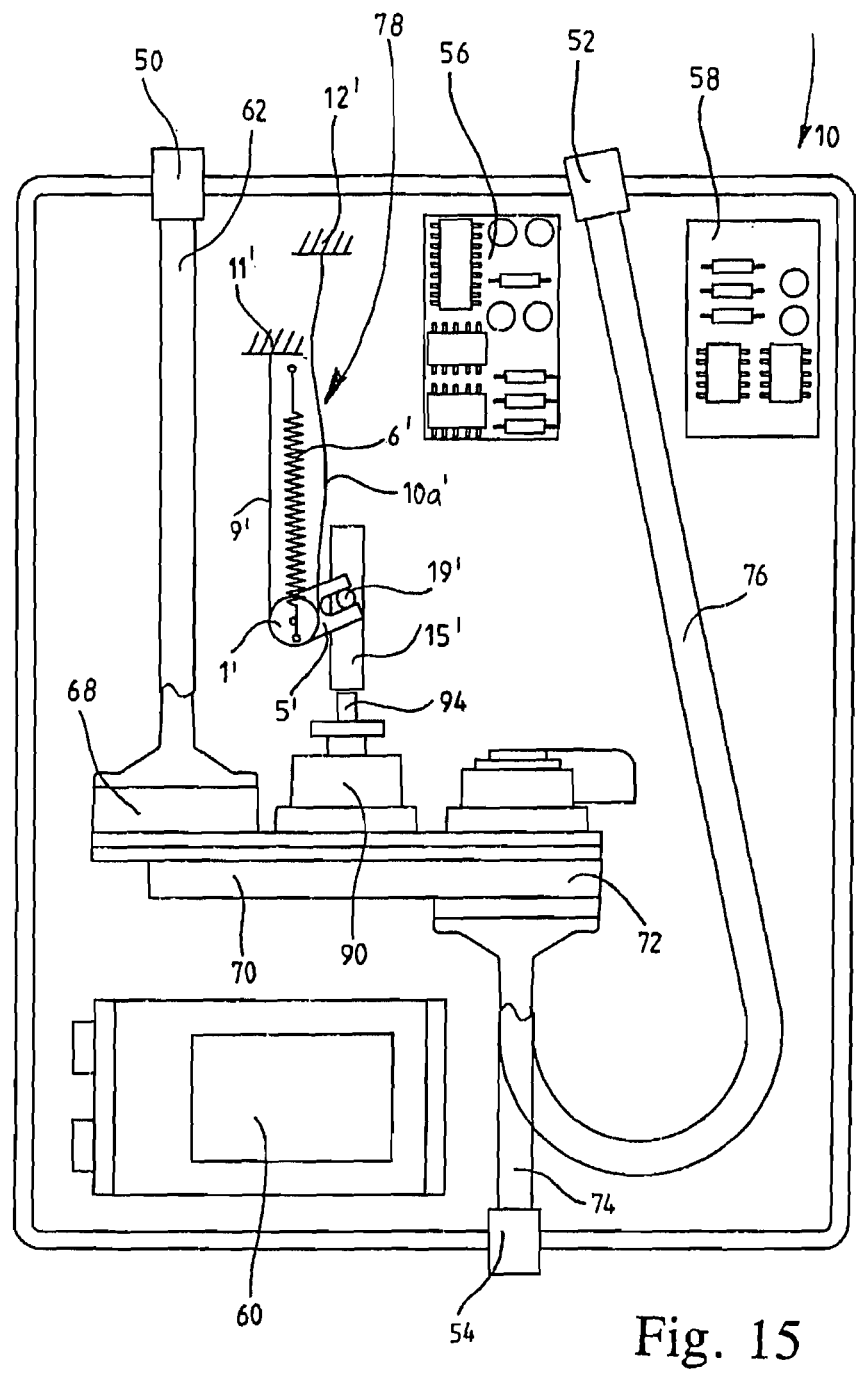
FIGS. 15 and 16 are schematic illustrations similar to FIG. 2 of a second embodiment of an infusion pump unit according to the invention illustrating the use of the shape memory alloy actuators of FIGS. 6-7 and FIGS. 10-12, respectively, as the pump actuators
Figure 16:
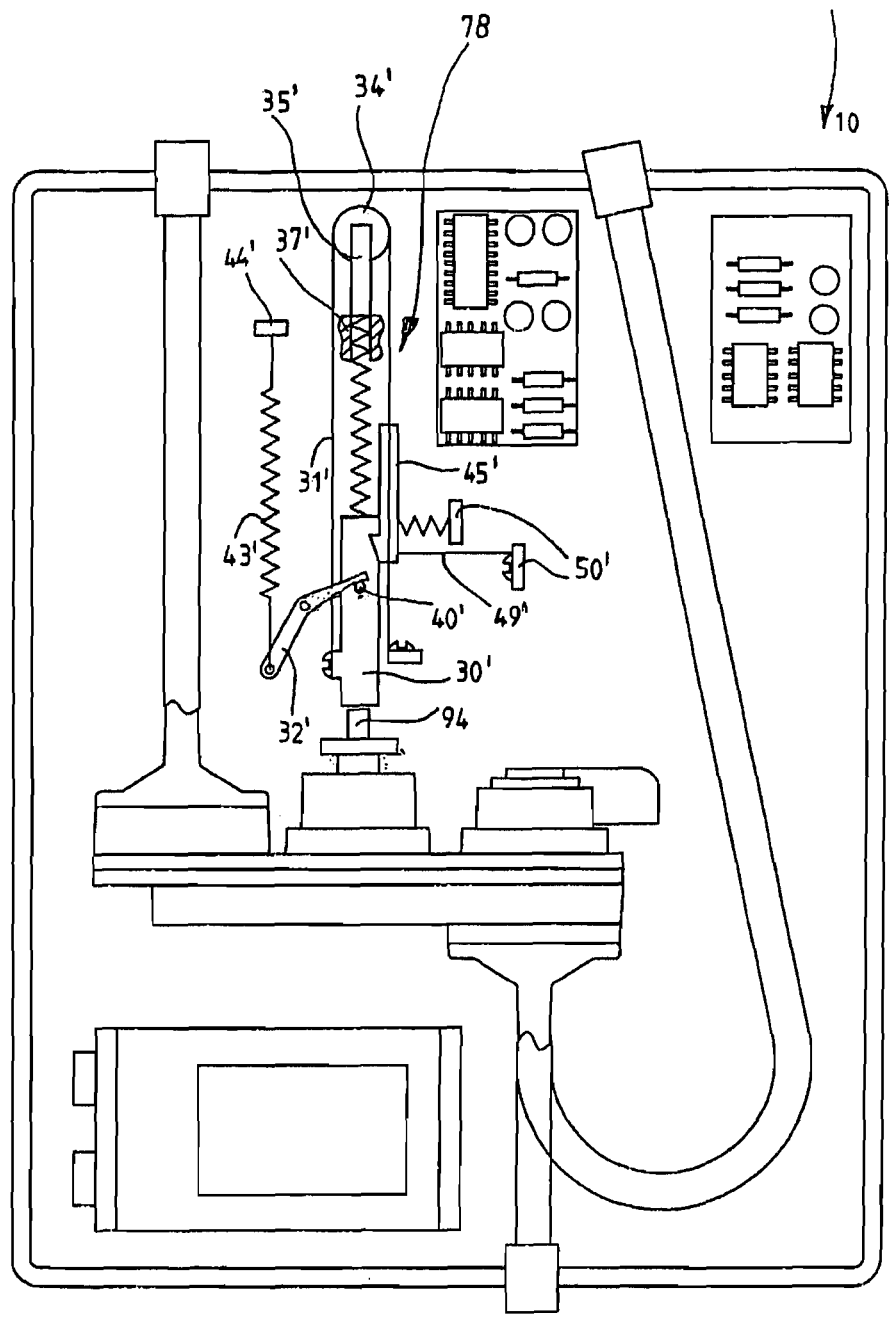

Referring now to FIGS. 15 and 16, the infusion pump unit 10 is very similar to the infusion pump unit 10 of FIG. 2, the sole difference being the location of the print cards 56 and 58. The actuators of FIGS. 6-7 and 10-12 are utilized as the pump actuator 78 in FIG. 15 and FIG. 16, respectively. The SMA wires are supplied with electrical current for heating by the battery pack 60

The SMA actuators of FIGS. 6-7 and 10-12 are particularly well-suited for depressing the pump membrane 92 (see FIG. 3) as the force needed for this operation increases as the membrane is depressed and the fluid is pressed out into the conduit 98. Furthermore, the operation of the SMA actuators is very quiet and the energy consumption is low while the space requirements are limited and the weight low.

As an example the SMA wire 31' of the SMA pump actuator of FIG. 16 is supplied with 4 amperes during 4 milliseconds for each pump depression cycle, and the maximum number of depression cycles for the infusion pump is normally of the order of magnitude of 10,000 cycles/hour.

Figure 17:
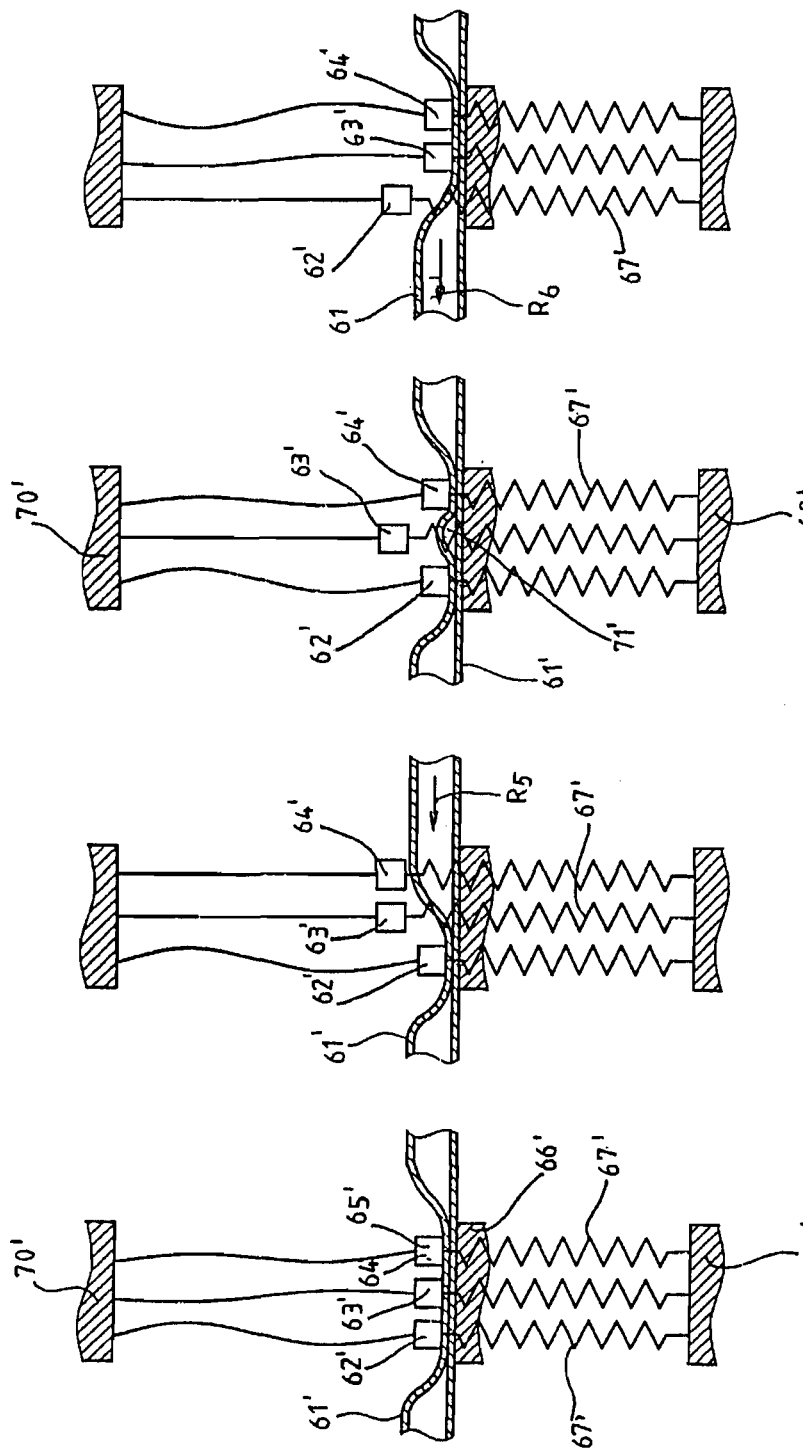
FIG. 17 is a sequence of schematic illustrations showing various stages in the pumping cycle of a fluid pumping system according to the invention utilising SMA actuators, FIG. 18 schematically illustrates two stages in the operation of an SMA actuator incorporated in the pumping system in FIG. 17.

Referring now to FIGS. 17 and 18, a fluid pumping system 60' comprises a flexible tube 61' extending through or between at least three clamping devices 62'-64' arranged adjacent one another. As illustrated in FIG. 18 the clamping devices each comprise a pivotable jaw 65' that is arranged to pivot towards a fixed jaw 66' to flatten the tube 61' extending between the jaws 65' and 66' and to pivot away from the fixed jaw 66' to allow the tube 61 to return to its natural open shape.

Each of the pivotable jaws 65' is attached to one end of a biasing means such as a tension spring 67' the other end of which is attached to a fixed portion 68' of a not shown frame. Each of the pivotable jaws 65' is furthermore attached to one end of a shape memory alloy wire 69' the other end of which is attached to a fixed portion 70' of said frame. The jaws 65' are held in the closed position against jaw 66' by the springs 67' with the tube 61' flattened while shortening or contraction of the SMA wires 69' opens the clamping devices by pivoting the jaws 65' away from the fixed jaw 66'.

The pumping action is achieved by the sequence indicated from left to right in FIG. 17, all three clamping devices 62'-64' being clamped shut in the first stage from the left with all three wires 69' cooled to below the transition temperature and therefore slack.

In the second stage from the left devices 63' and 64' are opened by heating the corresponding wires 69' to above the transition temperature whereby fluid enters the thus opened portion of the tube 61' as indicated by arrow R5.

In the third stage from the left device 64' is clamped shut by cooling the corresponding wire 69' such that the corresponding spring 67' can pull the corresponding jaw 65' against the tube 61' flattening it. Hereby a portion of fluid is trapped a space 71' in the tube 61'.

In the fourth stage from the left, the device 61' opens while the device 62' closes whereby the portion of fluid trapped in the space 71' is forced to flow in the direction of arrow R6 whereafter device 61' is closed and the first stage from the left has been re-established to begin a new pumping cycle.

If more than three clamping devices are utilized, the pumping effect will be enhanced.

This "finger" pump may substitute the pumping system in FIGS. 3, 15 and 16 as well as the check valves 68 and 72, and the pumping system (tube 61') may still be replaced without replacing the pump actuator by threading the tube 61' from between the jaws 65' and 66'. Thereby an extremely cheap replaceable pump is provided.

The pivoting of each of the jaws 65' of the clamping devices 62'-64' towards the fixed jaw 66' may be achieved by means of a body 15' of the actuator in FIG. 6 or a body 30' of the actuator in FIG. 5.

The tube 61' may alternatively be flattened directly by said bodies 15' or 30' without the use of a clamping device. Hereby, a particularly simple pumping system is achieved where the replacement of the tube 61' is particularly simple.

Figure 19:
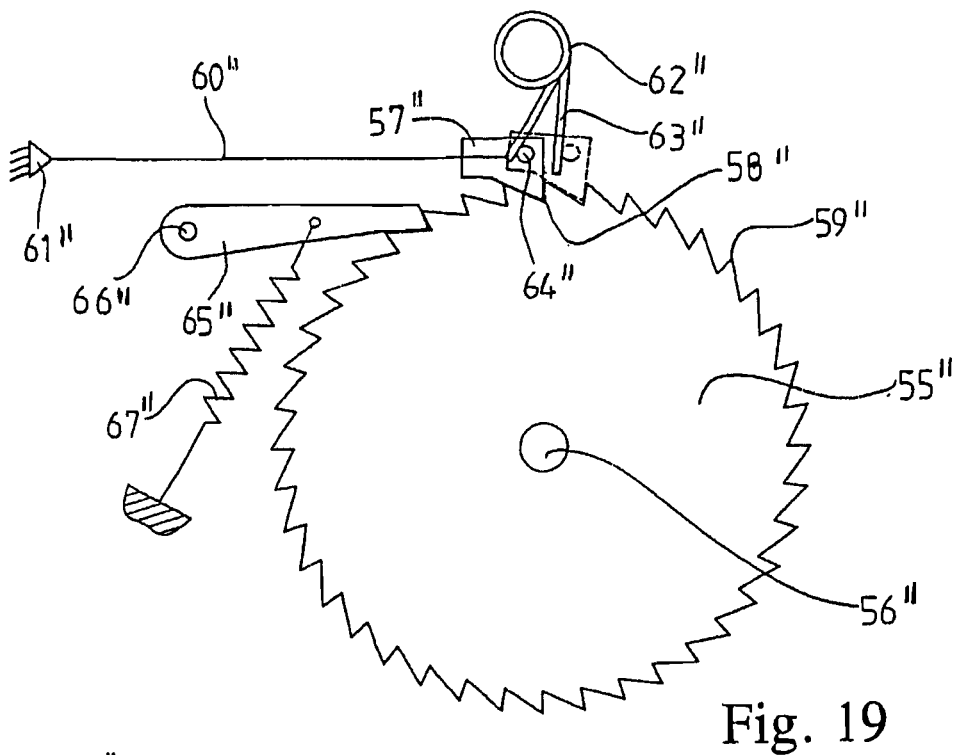
FIG. 19 is a schematic illustration of a first embodiment of a shape memory alloy actuator motor for use in an infusion pump according to the invention.

Referring now to FIG. 19, a toothed wheel or gear 55" is rotatably arranged on a power output shaft 56" journalled in a not shown frame of the actuator motor. A body 57" having an edge portion 58" fitting between two neighbouring teeth 59" of the gear 55" is arranged in said frame displaceable between the position shown in full lines and the position shown in dotted lines.

A shape memory alloy wire 60" is at one end attached to the body 57" and at the other end to a fixed portion 61" of said frame. A coiled flat or wire spring 62" integral with or connected to an arm 63" is attached to said frame such that said arm 63" may pivot around one end thereof opposite the free end thereof. The arm 63" abuts a pin 64" on the body 57".

A pawl 65" is pivotably arranged on a pivot 66" and is biased by a tension spring 67" so as to constantly abut the rim of the gear 55".

In use, the gear 55" is turned clock-wise by the body 57" being displaced from the full line position to the dotted line position thereof by the force of the spring 62" acting through the intermediate arm 63" on the pin 64", whereby the gear advances the width of one tooth 59" and the pawl 65" moves from locking engagement between one pair of teeth 59" to a locking position between the next pair of teeth in the counter clock-wise direction.

When the gear is locked against rotating counter clock-wise by the pawl 65", the SMA wire 60" is heated and shortens whereby the body is displaced from the dotted line position to the full line position against the force of the intermediate arm 63" on the pin 64" thereby cocking the spring 62".

The lever or moment arm of the displacement force exerted by the intermediate arm in the clock-wise direction with respect to the pivoting point of the arm decreases as the body is displaced in the activating direction from the full line position to the dotted line position whereby the displacement force exerted by the intermediate arm 63" on the pin 64" increases.

Figure 20:
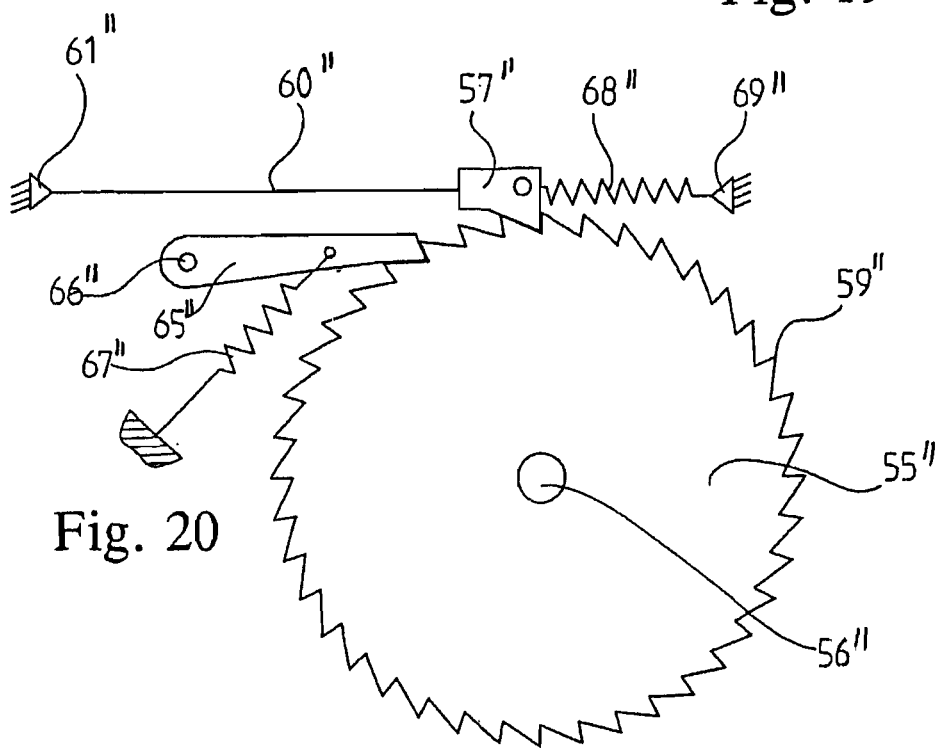
FIG. 20 is a schematic illustration of a second embodiment of a shape memory alloy actuator motor for use in an infusion pump according to the invention.

Referring now to FIG. 20, a SMA actuator motor similar to the motor of FIG. 19 is shown, the spring 62" and intermediate arm 63" being substituted by a tension spring 68" fastened to the body 57" and to a fixed portion 69" of a not shown frame.

The operation of the motor of FIG. 20 is very similar to the one in FIG. 19 except that the displacement force exerted on the body 57" by the spring 68" is exerted directly and declines substantially proportionally with the distance of displacement.

Figure 21:
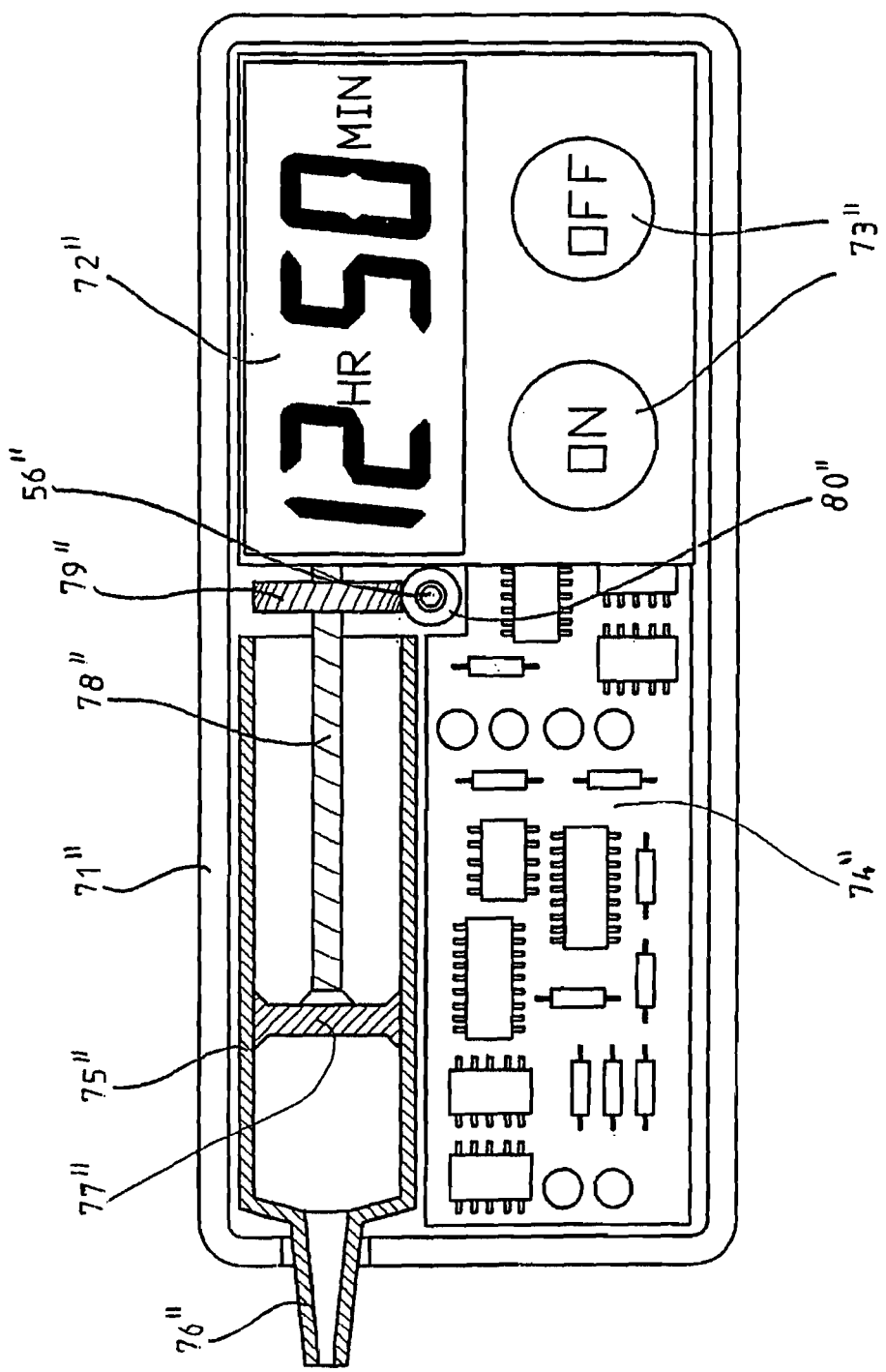
FIG. 21 is a schematic, partly sectional view of an infusion device according to the invention particularly well suited for dispensing insulin to a diabetes patient.

Referring now to FIG. 21, an infusion pump 70" particularly well suited for infusing insulin to a diabetes patient comprises a housing 71" containing a display 72", on/off buttons 73", print cards 74" and a not shown battery pack. These elements will not be described further as they are well known to those skilled in the art and may vary greatly within the scope of the invention as defined by the appended patent claims.

A dispensing cartridge, ampoule or syringe 75" is replaceably arranged in the housing 71" and has an outlet nozzle 76" for communication with a not shown conduit means connected to the patient for delivering the fluid, preferably insulin, in the syringe 75" to said patient in a controlled manner either continuously or according to a predetermined sequence.

A piston 77" is slidably arranged in the syringe 75". A threaded rod or spindle 78" abuts the piston 77" for displacing it towards the outlet nozzle 76" and meshes with a gear 79" meshing with a pinion 80" rotated by a shape memory alloy motor for displacing the spindle 78" towards the outlet nozzle 76".

Figures 22, 23:
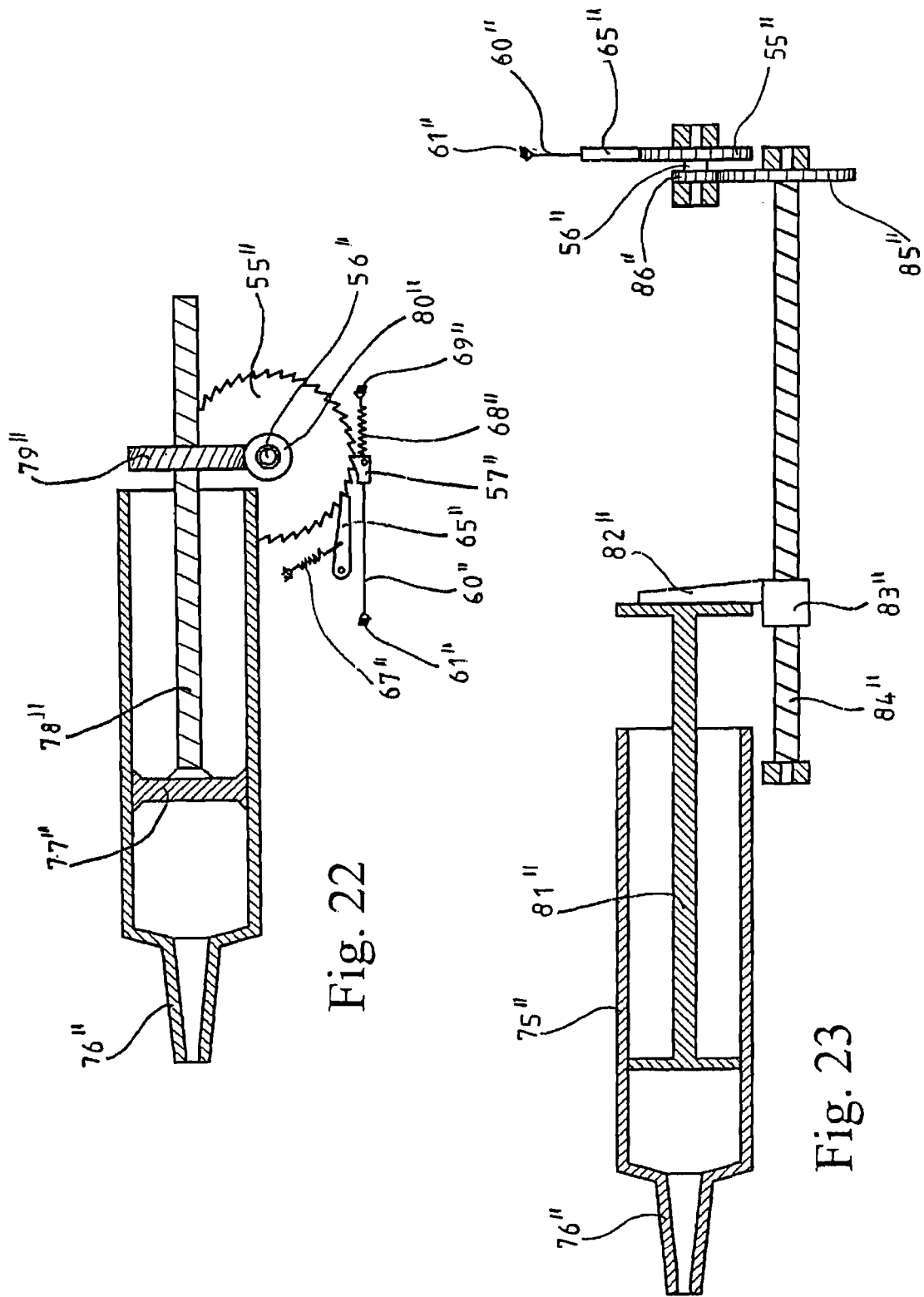
FIG. 22 is a schematic view of the actuator and dispensing syringe of the device in FIG. 21.
FIG. 23 is a schematic view of a second embodiment of an actuator and a dispensing syringe for incorporation in the device in FIG. 21

Referring now to FIG. 22, the SMA motor of FIG. 20 is shown arranged and adapted for rotating the pinion 80" such that rotation of the gear 55" is geared down to a much slower rotation of the spindle 78" so as to dispense the liquid or paste in the syringe 75" in very small amounts.

The SMA motor of FIG. 19 may very advantageously replace the motor of FIG. 19 in the configuration of FIG. 22 because of the reverse characteristic of the spring 62" compared to the characteristic of spring 68" as discussed in connection with FIGS. 13 and 14.

Referring now to FIG. 23, a different embodiment of the piston operation is illustrated, a double headed piston 81" being displaced by an arm 82" mounted on a carrier block 83" rotatably mounted on a spindle 84" such that rotation of the spindle 83" displaces the block 83", arm 82" and piston 81" towards the nozzle 76" for expelling liquid or paste in the syringe 75".

The spindle meshes with a gear 85" meshing with a pinion 86" attached to the shaft 56" of the SMA motor of FIG. 19, the spring 67" not being shown for the sake of clarity.

Figure 24:
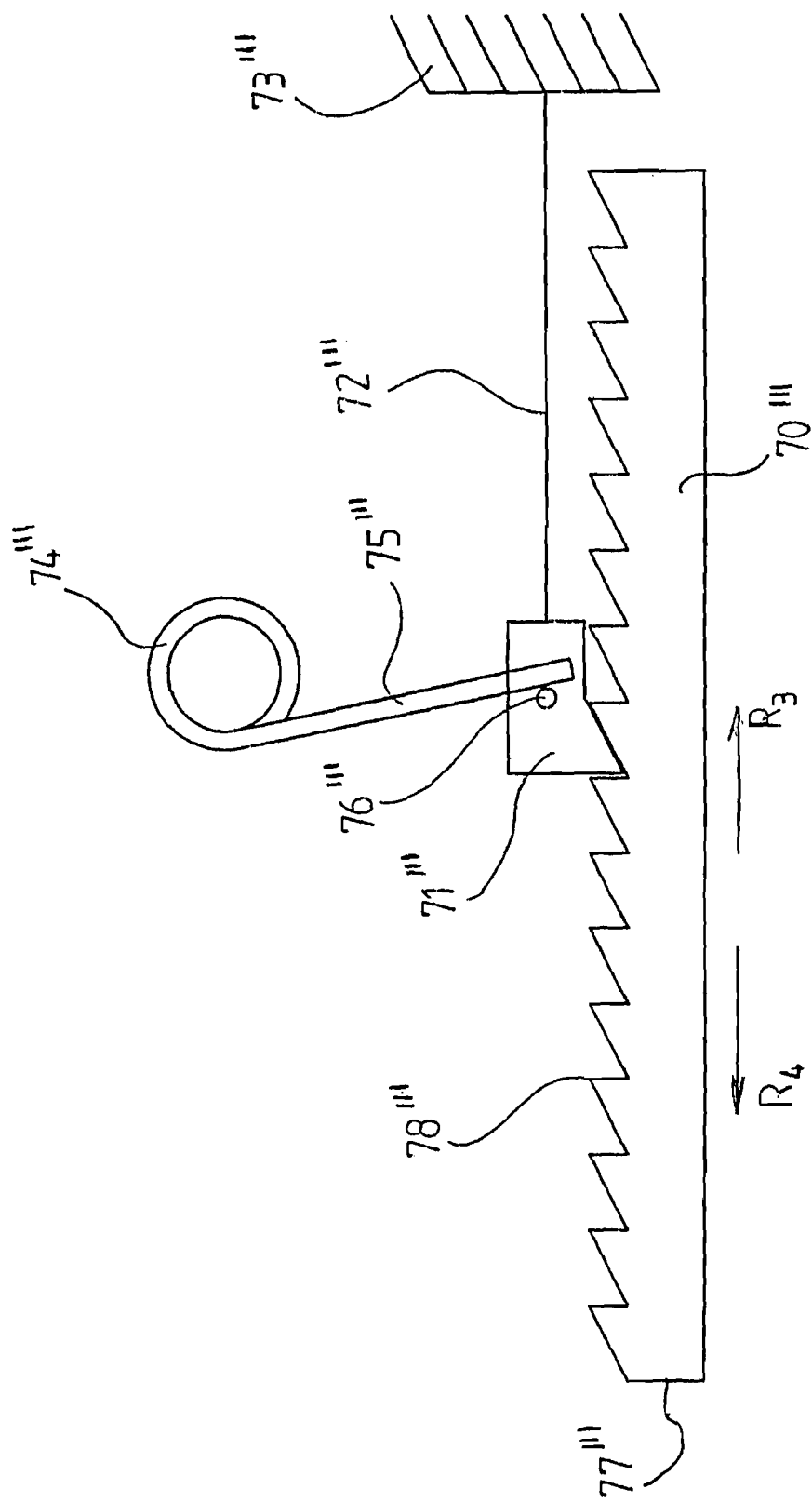
FIG. 24 is a schematic view of a rack-type SMA actuator for incorporation in the device in FIG. 21.

Referring now to FIG. 24, a rack 70''' is arranged displaceable in a not shown frame in the direction R4 and a body 71''' is arranged displaceable in the directions R3 and R4 as well as transversely thereto. A SMA wire 72''' is attached to the body 71''' and to a fixed portion 73''' of said frame. A coil spring 74''' attached to said frame and integral with or connected to an intermediate arm 75''' exerts a displacement force on a pin 76''' of the body 71''' through the intermediate arm 75''' in a manner very similar to spring 62" in FIG. 19.

The rack 70''' advances the distance of the width of one tooth 78''' thereof in the direction R4 for every cycle of heating and cooling of the SMA wire 72''' in the same way as gear 55" in FIG. 19 is rotated by wire 60", spring 62", intermediate arm 63" and body 57" in FIG. 19.

The rack 70" may be used to push the piston 77" in FIG. 22 or piston 81" in FIG. 23 by means of front end 77''', to empty said cylinder of liquid or paste through an aperture in said cylinder.

Figure 25:
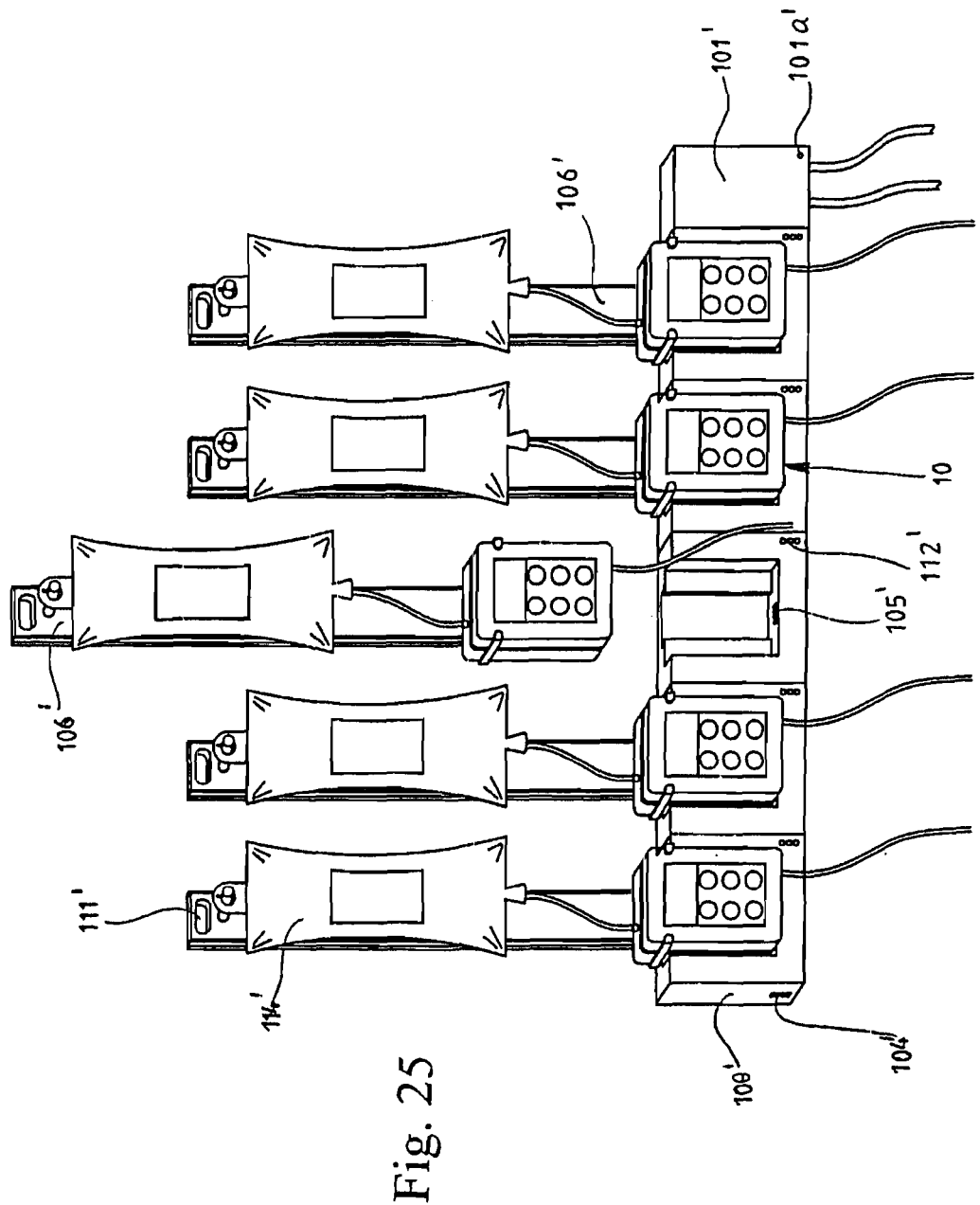
FIG. 25 is a perspective and schematic view illustrating an alternative application of the first embodiment of the portable infusion pump unit illustrated in FIGS. 1-4 in a stationary charger and fixation system for providing a stationary infusion pump system.
Figure 26:
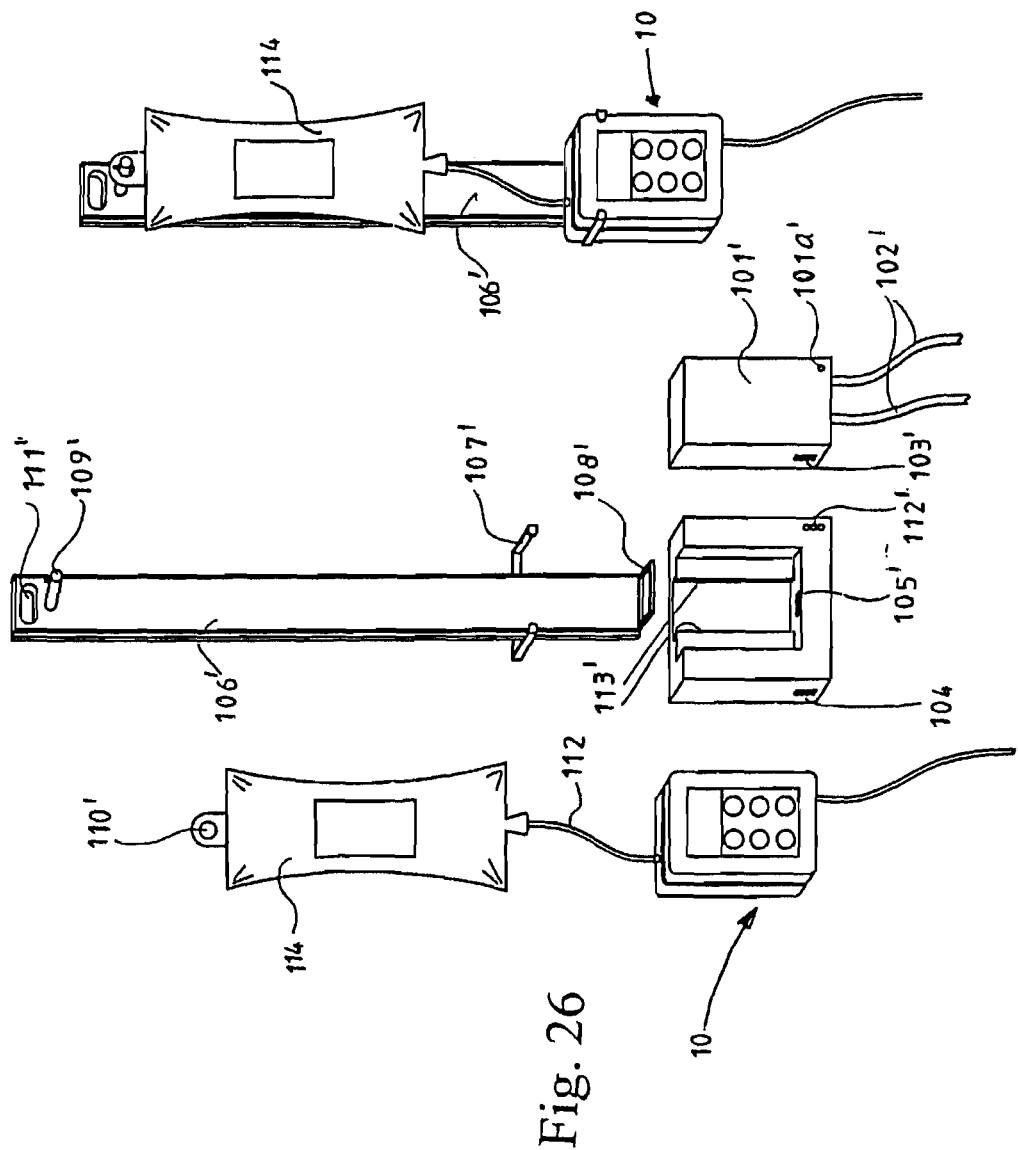
FIG. 26 is a perspective and schematic view of the components of the system in FIG. 25.

Referring now to FIGS. 25 and 26, an optional number of infusion pump units 10 with corresponding inlet tube 112 and infusion bag 114 may be aggregated in a system of individual docking stations 100' arranged on a not shown standard hospital rack allowing horizontally adjustable location of the docking stations 100' that such two or more stations may be aligned abutting one another as shown in FIG. 25.

A power distribution and computer connection box 101' having connections 102' to a power source and a computer is also adapted for abutting a docking station 100' in aligned configuration therewith.

The distribution box 101' has a number of female contact plugs 103' for mating with corresponding, not shown, male contact plugs in a lateral wall of a docking station 100'. A diode 101a' indicates whether the distribution box is functioning or not. Each docking station has a number of female contact plugs 104' in the opposite lateral wall identical to contact plugs 103' for mating with said not shown male contact plugs of an adjacent docking station 100'.

The female and male contact plugs distribute electrical energy to the individual docking station and to the individual infusion pumps 10 docked in the docking stations 100' via female contact plugs 105' mating with not shown corresponding male contact plugs in the bottom of each infusion pump 10.

Each infusion pump 10 is carried by a carrying frame 106' between arms 107' thereof and supported on a bottom platform 108' thereof. A hook 109' is provided on the carrying frame 106' for hooking into an aperture 110' of the infusion bag 114. The frame 106 furthermore has a top aperture 111' for receiving a hook on a bed or wheel chair when the pump 10 and bag 114 are to be removed from the docking station 100' for following a patient away from the fixed docking station array.

Each docking station 100' is provided with three diodes 112' for indicating status of the docking station and the pump as regards power supply, pumping status and fluid supply or other parameters desired monitored. Each docking station furthermore has two opposed grooves for slidingly receiving the lateral edges of a frame 106'

The system of FIG. 25 affords great flexibility as to number of infusion pumps per patient and as regards mode of transport together with the patient either on the frame 106' or removed therefrom.

The invention claimed is:

1. An infusion pump device, comprising:
   a portable pump housing defining a space to receive insulin;
   a user interface engaged with the portable pump housing, the user interface comprising a display device that shows data to a user;
   a piston rod defining an exterior thread pattern and linearly movable in an axial direction in the housing to advance from a first position to a second position so as to dispense insulin from the pump housing when insulin is received in the pump housing;
   a ratchet mechanism to urge the piston rod from the first position to the second position;
   a gear that is rotatable in an activation direction to drive the piston rod from the first position to the second position, wherein the ratchet mechanism comprises a ratchet body that engages the gear, the ratchet body being adjustable from a non-activating position to an activating position so as to incrementally rotate the gear in the activation direction, and wherein the ratchet body maintains physical contact with the gear when moving between the non-activating position and the activating position; and
   a spring device that provides a drive force to the ratchet mechanism to advance the piston rod to the second position and thereby dispense insulin from the pump housing by mechanical power of the spring device when insulin is received in the pump housing.

2. The infusion pump device of claim 1, wherein the ratchet mechanism further comprises a pawl device that engages the gear to prevent rotation of the gear in a direction opposite the activation direction.

3. The infusion pump device of claim 1, wherein the spring device urges the ratchet body from the non-activating position to the activating position so that the piston rod is advanced to the second position by the mechanical power of the spring device.

4. The infusion pump device of claim 1, further comprising an electrically-actuated shape memory device that provides a reset displacement force to the ratchet mechanism.

5. The infusion pump device of claim 4, wherein the shape memory device shortens when heated by electrical current so as to exert the reset displacement force upon the ratchet mechanism.

6. The infusion pump device of claim 4, wherein the spring device is cocked when the shape memory device exerts the reset displacement force upon the ratchet mechanism.

7. The infusion pump device of claim 1, wherein the spring device comprises at least one device selected from the group consisting of a tension spring, a compression spring, a flat spring, and a piston-and-cylinder mechanism.

8. The infusion pump device of claim 1, wherein the display device shows data related to insulin treatment.

9. The infusion pump device of claim 1, wherein the user interface further comprises one or more buttons for actuation.

10. The infusion pump device of claim 1, further comprising a battery power source disposed in the pump housing.

11. The infusion pump device of claim 1, wherein the pump housing defines the space to receive a separate insulin container.

12. The infusion pump device of claim 1, wherein the piston rod is movable in the housing to dispense the insulin from the pump housing according to a predetermined sequence when the insulin is received in the pump housing.

13. The infusion pump device of claim 1, wherein the exterior thread pattern of the piston rod mates with an internal thread pattern of a driver gear so that rotation of the driver gear causes linear advancement of the piston rod.

14. The infusion pump device of claim 1, wherein the gear is a first gear that mates with a second gear having a different size, the second gear engaging with the piston rod to advance from the piston rod from the first position to the second position when the first gear is rotated in the activation direction.

15. The infusion pump device of claim 1, wherein the gear is indirectly coupled to the piston rod via a gear reduction arrangement.

16. A method for dispensing insulin from a portable infusion pump device, the method comprising:
    receiving input via a user interface that is engaged with a portable pump housing that defines a space containing insulin, the user interface comprising a display device that shows data related to insulin treatment and a plurality of buttons for actuation;
    providing a drive force from a spring device to a ratchet mechanism that engages a gear arranged in the portable pump housing, the ratchet mechanism comprising a ratchet body that is adjustable from a non-activating position to an activating position when the drive force is provided by the spring, wherein the ratchet body maintains physical contact with the gear when moving between the non-activating position and the activating position; and
    advancing a piston rod under mechanical power from the spring device from a first position to a second position so as to dispense the insulin from the pump housing, the piston rod being linearly moved in an axial direction in the housing and being urged to the second position when the spring device provides the drive force to adjust the ratchet body from the non-activating position to the activating position.

17. The method of claim 16, wherein the piston rod comprises an external thread pattern that mates with an internal thread pattern of a driver gear so that rotation of the driver gear causes linear advancement of the piston rod.

18. The method of claim 16, wherein the display device of the user interface shows timing data.

19. The method of claim 16, providing a reset displacement force from an electrically-actuated shape memory device to the ratchet mechanism.

20. An infusion pump device, comprising:
    a portable pump housing defining a space to receive insulin;
    a user interface engaged with the portable pump housing, the user interface comprising a display device that shows data to a user;
    a piston rod defining an exterior thread pattern and movably arranged in the housing to advance from a first position to a second position so as to dispense insulin from the pump housing when insulin is received in the pump housing;
    a ratchet mechanism to urge the piston rod from the first position to the second position;
    a gear that is rotatable in an activation direction to drive the piston rod from the first position to the second position, wherein the ratchet mechanism comprises a ratchet body that engages the gear, the ratchet body being adjustable from a non-activating position to an activating position so as to incrementally rotate the gear in the activation direction, and wherein the ratchet body maintains physical contact with the gear when moving between the non-activating position and the activating position;

a pawl that is pivotably arranged on a pivot and is biased by a tension spring so as to constantly abut a rim of the gear; and a spring device that provides a drive force to the ratchet mechanism to advance the piston rod to the second position and thereby dispense insulin from the pump housing by mechanical power of the spring device when insulin is received in the pump housing.

21. The infusion pump device of claim 20, wherein the spring device urges the ratchet body from the non-activating position to the activating position so that the piston rod is advanced to the second position by the mechanical power of the spring device.

22. The infusion pump device of claim 20, further comprising an electrically-actuated shape memory device that provides a reset displacement force to the ratchet mechanism.

23. The infusion pump device of claim 20, wherein the display device shows data related to insulin treatment.

24. The infusion pump device of claim 20, wherein the user interface further comprises one or more buttons for actuation.

25. The infusion pump device of claim 20, further comprising a battery power source disposed in the pump housing.

26. The infusion pump device of claim 20, wherein the pump housing defines the space to receive a separate insulin container.

27. The infusion pump device of claim 20, wherein the gear is a first gear that mates with a second gear having a different size, the second gear engaging with the piston rod to advance from the piston rod from the first position to the second position when the first gear is rotated in the activation direction.

28. The infusion pump device of claim 20, wherein the gear is indirectly coupled to the piston rod via a gear reduction arrangement.

* * * * *

UNITED STATES PATENT AND TRADEMARK OFFICE
CERTIFICATE OF CORRECTION

| | | |
|---|---|---|
| PATENT NO. | : 8,597,244 B2 | Page 1 of 1 |
| APPLICATION NO. | : 11/738311 | |
| DATED | : December 3, 2013 | |
| INVENTOR(S) | : Morten Mernoe | |

It is certified that error appears in the above-identified patent and that said Letters Patent is hereby corrected as shown below:

In the Specifications

In Column 1, Line 8 (approx.), delete "7,242,423," and insert --7,232,423,--, therefor.

In Column 1, Line 11 (approx.), delete "Apr. 24, 2002." And insert --Jul. 24, 2002.--, therefor.

Signed and Sealed this
Eighteenth Day of March, 2014

Michelle K. Lee
*Deputy Director of the United States Patent and Trademark Office*